(12) United States Patent
Morita

(10) Patent No.: US 6,266,141 B1
(45) Date of Patent: Jul. 24, 2001

(54) BIREFRINGENCE MEASURING APPARATUS AND METHOD OF MEASURING BIREFRINGENCE

(75) Inventor: Nobuhiro Morita, Yokohama (JP)

(73) Assignee: Ricoh Company, Ltd., Tokyo (JP)

( * ) Notice: Subject to any disclaimer, the term of this patent is extended or adjusted under 35 U.S.C. 154(b) by 0 days.

(21) Appl. No.: 09/296,129

(22) Filed: Apr. 22, 1999

(30) Foreign Application Priority Data

Apr. 22, 1998 (JP) .................................................. 10-111813
Apr. 22, 1998 (JP) .................................................. 10-111814
Jul. 23, 1998 (JP) .................................................. 10-207764

(51) Int. Cl.[7] ........................................................ G01J 4/00
(52) U.S. Cl. .................................................. 356/365; 356/368
(58) Field of Search ............................. 356/365, 364, 356/368; 250/225

(56) References Cited

U.S. PATENT DOCUMENTS

| | | | |
|---|---|---|---|
| 3,811,775 | * 5/1974 | Abu-Saud | .............................. 356/365 |
| 5,257,092 | * 10/1993 | Noguchi et al. | ....................... 356/367 |
| 5,457,536 | * 10/1995 | Kornfield et al. | ..................... 356/368 |
| 5,504,581 | * 4/1996 | Nagata et al. | .......................... 356/365 |
| 5,521,705 | * 5/1996 | Oldenbourg et al. | ................. 356/368 |

FOREIGN PATENT DOCUMENTS 1-232238 * 9/1989 (JP) ....................................... 356/327

* cited by examiner

Primary Examiner—F. L. Evans
Assistant Examiner—Zandra V. Smith
(74) Attorney, Agent, or Firm—Oblon, Spivak, McClelland, Maier & Neustadt, P.C.

(57) ABSTRACT

Transmission light from a detection lens is directed to a polarization element as incident light. The polarization element is rotated, and the light is received and detected by an array-state light-receiving element, and the birefringence of the detection lens is calculated. The distance between a lens for radiating the diffusion light onto the detection lens and the detection lens itself can be optionally set. Observing the transmission image of the detection lens, the distance between the detection lens and the lens is determined. Thereby, it is possible to obtain optical elasticity interference fringes which at most are scarcely affected by optical distortions. In addition, a focusing magnification rate is most suitably set to match states of birefringence occurrence which are different in accordance with the detection lens or the placement thereof. A compensation optical system composed of a lens respectively has different focal distances f1 and f2 in the main scanning direction and in the subscanning direction, and can be added into a space between the radiation optical system and the detection lens. The light from the detection lens is substantially parallel.

57 Claims, 18 Drawing Sheets

BIREFRINGENCE MEASURING APPARATUS AND METHOD OF MEASURING BIREFRINGENCE

BACKGROUND OF THE INVENTION

1. Field of the Invention

The present invention relates to an apparatus for and a method of measuring the birefringence of a detection lens, such as plastics lens, etc. for use in the writing-in or picking-up of a light utilized in a laser printer, etc.

2. Discussion of the Background Art

Up to now, as to a method of measuring the birefringence of a detection object such as a detection lens, etc., a phase modulating method and a rotative analyzer method have been well known. In those methods, parallel light beams are radiated onto a transparent detection object. A transmission light from the detection object is received by a light-receiving element such as a photodiode, etc. The variation of the polarization state of the transmission light due to the birefringence of the detection object is detected, and thereby the birefringence of the detection object can be obtained.

Regarding the phase modulation method, as reported in one background art document "Measurement of Birefringence utilizing the Phase Modulation Method, and Application thereof" on pages 127–134, in OPTICAL TECHNOLOGY CONTACT, Vol. 27, No. 3 (1989), the phase of the radiation light is modulated by use of an optical-elasticity modulator (PEM). The birefringence thereof is obtained from the phase between the beat signal of the light transmitted through the transparent detection object and the modulation signal.

Regarding the rotative analyzer method, as reported in "Polarization Analysis" on pages 256–265, in OPTICAL MEASUREMENT HANDBOOK—Asakura Bookstore (published on Jul. 25, 1981) edited by Toshiharu Takoh, Junpei Tsujiuchi, and Shingeo Minami, etc., an analyzer which is put on a rear surface of the transparent detection object is rotated, and the transmission light is received at the same time by a light-receiving element on the rear surface of the analyzer. The birefringence thereof can be obtained by the variation of the received light output from the light-receiving element due to the rotation of the analyzer.

Furthermore, according to still another background-art document, published specifications of Japanese Laid-open Patent Publication Nos. 4-58138/1992 and 7-77490/1995, enlarged parallel light is radiated onto the transparent detection object and the transmission light transmitted therethrough is received by a two-dimensional sensor. In such a way, the birefringence of the detection object can be obtained, and thereby the surface (two-dimensional) measurement of the birefringence can be realized.

In any one of the phase modulation method and the rotative analyzer method, a so-called "point measurement" is utilized. Namely, fine parallel light beams are radiated onto the detection object and the light beams thus radiated are received by a photodiode, for example. Therefore, in order to measure the entire surface of the detection object, it is necessary to adjust the detection object and the measurement apparatus for measuring the detection object. Especially, in a case that the detection object is a non-flat plate such as a lens, since the light beam radiated onto the detection lens is refracted by the detection lens, the setting operation for the detection object or the measurement apparatus turns out to be very difficult.

Furthermore, according to the published specification of Japanese Laid-open Patent Publication No. 4-58138/1992, the adjustment of the detection object, etc. is not necessary, because of the "two-dimensional" measurement. However, in the case of using a lens having a large diameter such as a writing-in lens (usually an fθ lens) for use in a laser printer, etc., the difference between the refractive indexes at the center portion and a circumferential edge portion of the lens is large, and thereby optical distortion tends to occur very often after transmitting the light.

For instance, FIG. 18 shows a structure of a measurement optical system in which the object lens 301 is disposed with a detection lens 300 to construct a focal system. In FIG. 18, collimation light beams 302 are radiated onto the detection lens 300. The light transmitted through the detection lens 300 is collimated by the object lens 301, and thereafter the light thus collimated is guided to the light-receiving element side through a polarization element as the measurement light 303, and then the light thus guided is received by a light-receiving element. The measurement is performed on the basis of the light-receiving output.

On this occasion, the refraction force or the degree of refraction of the light rays 302c passing through the center portion of the detection lens 300 differs from that of the light rays 302e passing through the circumferential edge portion thereof. As a result, in the case of arranging both of the lenses 300 and 301 so as to cause the focuses thereof to coincide with each other, and even if the aberration of the object lens 301 is very small as an ideal lens, the light rays 302e transmitted through the circumferential edge portion of the detection lens 300 are directed toward the side of the light-receiving element as the superposing measurement light 303e. Therefore, it is impossible to obtain clear optical elasticity interference stripe images over an entire surface of the detection lens 300.

FIG. 19 shows an example in which, as the optical elasticity interference stripe images 305 obtained on the light-receiving element 304 in the measurement optical system as shown in FIG. 18, an edge portion 305e of the image 305 becomes brighter than at other portions thereof by the influence of the measurement light 303e due to the superposed light rays, or there exists a portion 306 affected by the stray light. In such a situation, it is difficult to measure the extremely bright portion 305e or the other portions 306 affected by the puzzling light.

In a case as shown in FIG. 20 that a light writing-in lens 400 for use in a laser printer, etc. is the detection lens, in the practical use, the light rays transmitted through the light writing-in lens 400 do not become parallel with the optical axis of the optical system on many occasions, for instance. The example shown in FIG. 20 is an exposure scanning system in which the image surface on the photosensitive body 406 surface is exposed with the light and scanned by the laser light emitted from the semiconductor laser unit 401 through a collimator lens 402, a polygon mirror 403, lenses 404 and 405, and the light writing-in lens 400. Consequently, if the birefringence measurement is practiced with the setting of the measurement optical system so as to make the light rays passing through the light writing-in lens 400 (as a detection lens) parallel with the optical axis of the optical system, the transmission path of the light rays transmitted through the light writing-in lens 400 turns out to largely differ from that in the state of its practical use.

Since the amount of the birefringence is largely changed in accordance with the transmission path of the light rays, it is desirable to practice the measurement of birefringence in the state near the practical use of the light writing-in lens 400. Furthermore, if the transmission light of the detection lens does not become parallel with the optical axis of the optical system, the light is directed slantedly toward the polarization element as the incident light. This results in a measurement error because the polarization has, in general, incident angle dependability.

SUMMARY OF THE INVENTION

The present invention has been made in order to solve the above-mentioned and other problems. Therefore, some objects of the present invention are as follows.

It is an object of the present invention to solve the problems of the background art as mentioned heretofore.

It is another object of the present invention to obtain a transmission image transmitted through a detection lens scarcely affected by optical distortion.

It is still another object of the present invention to precisely perform birefringence measuring over an entire surface of a detection lens.

It is still another object of the present invention to provide a birefringence measuring apparatus and birefringence measuring method capable of obtaining a transmission image transmitted through a detection lens scarcely affected by optical distortion, precisely performing the birefringence measuring over the entire surface of the detection lens, and easily dealing with a change of a type of detection lens and improving the general usefulness.

It is still another object of the present invention to provide a birefringence measuring apparatus and a birefringence measuring method capable of precisely performing the measurement over an entire surface of a detection lens with small measurement error even in a case of using a detection lens such as a light writing-in lens.

It is still another object of the present invention to provide a birefringence measuring apparatus in which a compensation optical system including a lens having different focal distances in a main scanning direction and a subscanning direction is added when the focal distances of a detection lens are different from each other in both of the directions, and thereby the transmission can be made almost parallel.

It is still another object of the present invention to provide a birefringence measuring apparatus capable of widening a width of coping with a change of a type of a detection lens by combining an axis-asymmetrical lens with a general axis-asymmetrical lens.

It is still another object of the present invention to provide a birefringence measuring apparatus and a birefringence measuring method which can divide and measure an area of an entire detection lens.

Furthermore, it may be desired that a distance between an optical system for radiating light onto a detection lens and a detection lens itself is enabled to be optionally set, and observing the transmission image of the detection lens the distance between the detection lens and the spot light source (focal point of an object lens in a microscope) is adjusted, and thereby, it is possible to obtain the transmission image of the detection lens (optical elasticity interference stripe images) scarcely affected by optical distortion, and therefore, the birefringence can be precisely measured over the entire surface of the detection lens, and at the same timer it turns out to be possible to easily cope with a change of a type of the lens and improve the wide usefulness.

The above-mentioned matter is further described in more detail. In a recent lens for use in a writing-in optical system, lenses respectively having different focal points in the main scanning direction and the subscanning direction (in the lengthwise and widthwise directions of the lenses for use in the scanning optical system) are used on some occasions. In the case of measuring the birefringence of such lenses, it is difficult to make parallel (collimate) the transmission light transmitted through the detection lens by radiating spherical surface waves symmetrical from the axis onto the detection lens.

If the light flux transmitted through the detection lens is not parallel light flux, the light is slantedly directed as incident light onto a polarization element surface disposed immediately before the light-receiving element. However, since the polarization element does not operate normally when the light is not directed almost perpendicularly to its surface, a measurement error occurs inevitably.

Furthermore, in such an above-mentioned apparatus, the measurement is performed in such a state that the vicinity of the detection lens surface and the surface to the light receiving element are put almost in the focusing relationship (namely, a focused image is obtained in the vicinity of the detection lens surface). However, if the focal distances of the detection lens are different from each other in the main scanning direction and the subscanning direction, the focusing positions differ from each other in both scanning directions, and thereby a distorted image is obtained on the light receiving element. As the result, regarding the measurement values on the detection lens surface and on the obtained image surface, it is impossible to take the correspondence of the positions on both surfaces.

In consideration of the above-mentioned matters, in the present invention, when the focal distances of the detection lens are different from each other, for instance, in the main scanning direction and the subscanning direction, a compensation optical system including a lens having different focal distances in the main scanning direction and the subscanning direction is added to the radiation optical system. In such a structure, the transmission light transmitted through the detection lens can be made almost parallel. The present invention enables coping with the above-mentioned requirements by adopting a structure as mentioned heretofore. Thus, the present invention provides the birefringence measuring apparatus of further wide usefulness.

Furthermore, the present invention provides a birefringence measuring apparatus capable of widening a width of coping with a change of the type of the detection lens by combining an axis-asymmetrical lens with a general axis-symmetrical lens even in a case that the focal distance of the detection lens is long, and thereby the present invention is capable of further raising the wide usefulness of the measurement.

Furthermore, when a focal distance of the detection lens is long, the distance between the detection lens and the radiation optical system has to be taken long. However, if such a long distance is required, the apparatus becomes large-sized inevitably. For this reason, assuming that the detection lens is almost a parallel flat plate (namely, the curvature of the lens surface is infinite), it can be thought that the radiation light emitted from the radiation optical system is previously converted to a parallel light flux, and thereafter, the converted parallel light flux is radiated onto the detection lens. However, on this occasion, when the entire area of the detection lens is intended to be measured, it is necessary to radiate the parallel light flux of large diameter (diameter larger than the diameter of the detection lens) to the extent of covering the entire detection lens.

However, in order to uniformly make parallel (collimate) the entire light flux of a diameter which is large to the extent of exceeding the diameter of the detection lens, it is necessary to use a complicated and high-cost optical system, and thereby the manufacturing costs rise up inevitably. Consequently, it may become difficult to divide and measure an area of an entire detection lens by moving the light receiving element side.

Here, in the present invention, even in a case that the focal distance of the detection lens is long, the detection lens is moved in a direction substantially perpendicular to the optical axis of the optical system, and thereby, the area of the entire detection lens can be divided and measured. The present invention thus provides a birefringence measuring apparatus and a method of measuring the birefringence which enables a dividing and measuring the area of the entire detection lens in such a manner as mentioned above.

Other objects, features and advantages of the present invention will become apparent from the following detailed description when read in conjunction with the accompanying drawings.

BRIEF DESCRIPTION OF THE DRAWINGS

A more complete appreciation of the present invention and many of the attendant advantages thereof will be readily obtained as the same becomes better understood by reference to the following detailed description when considered in connection with the accompanying drawings, wherein:

FIG. 15 is a diagram for explaining an operation of a compensation optical system, wherein

DESCRIPTION OF THE PREFERRED EMBODIMENTS

Figure 1:
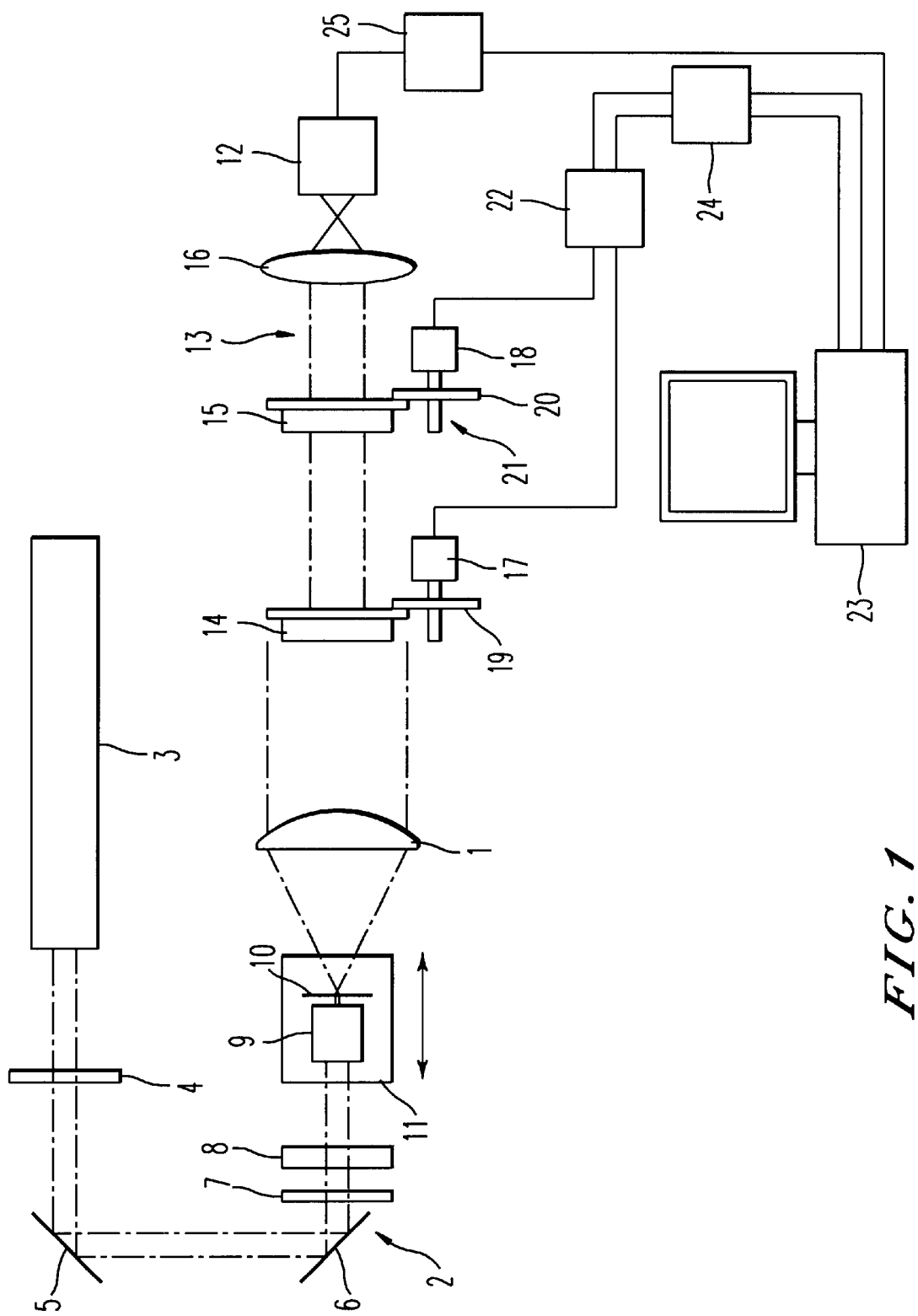
FIG. 1 is a structural view showing a first embodiment according to the present invention.

In describing preferred embodiments of the present invention illustrated in the drawings, specific terminology is employed for the sake of clarity. However, the present invention is not intended to be limited to the specific terminology so selected and it is to be understood that each specific element includes all technical equivalents which operate in a similar manner.

Referring now to the drawings, wherein like reference numerals designate identical or corresponding parts throughout the several views, there are illustrated an apparatus for a method of measuring the birefringence of a detection lens such as plastics lens, etc. for use in a writing-in or picking-up of light utilized in a laser printer, etc.

FIRST EMBODIMENT

A first embodiment of the present invention is described hereinafter, referring to FIG. 1 and FIG. 2. A detection lens 1, as an object to be measured in the first embodiment is held by a holder (not shown). At first, a radiation optical system 2 for radiating light onto the detection lens 1 in a predetermined polarization state is provided for such detection lens 1.

The above-mentioned radiation optical system 2 is constructed with a He—Ne laser 3 employed as a light source for emitting a light beam of random polarization, an ND filter for adjusting the light intensity, deflection mirrors 5 and 6, and a polarization plate 7 for converting the light from the He—Ne laser 3. The radiation optical system 2 further includes a straight-line polarization light, a λ/4-plate 8 for further converting the straight-line polarization light converted by the polarization plate 7 to a circular polarization light, a lens 9, and a pin hole 10.

The lens 9 equally serves as an object lens of a microscope and radiates diffusion light toward the detection lens 1. The pin hole 10 functions as a spatial filter. The lens 9 and the pin hole 10 are carried on a stage 11 capable of moving in the optical axis direction. The lens 9 and the pin hole 10 are moved back and forth in the optical axis direction by the rotative action of a stepping motor (not shown) for driving the stage 11.

Here, a radiation-side displacement medium is constructed with the stage 11, the stepping motor, etc., and the position of the lens 9 in the optical axis direction from the detection lens 1 can be adjusted. Furthermore, a position sensor for sensing a rotation origin (starting-point) is provided on the stepping motor. The distance between the lens 9 and the detection lens 1 is previously set to a predetermined distance. Assuming that the state position is decided as the movement origin of the stage 11, the variation of the distance between the lens 9 and the detection lens 1 caused by the movement of the stage 11 can be detected, by counting the number of pulses supplied to the stepping motor.

Furthermore, a CCD camera 12 serving as an array-state light-receiving element for receiving transmission light is provided on the optical axis at the transmission/emission side of the detection lens 1. A focusing optical system 13 is provided between the detection lens 1 and the CCD camera 12.

The focusing optical system 13 is constructed with a $\lambda/4$-plate 14 for converting a light flux of elliptic polarization approximated to circular polarization to a light flux of elliptic polarization approximated to straight-line polarization by action of the birefringence at the time of passing through the detection lens 1, and a focusing lens 16 for focusing the light passing through the polarization plate 15 serves as a polarization element. The position of the lens 16 is adjusted such that a focusing relationship is established between the lens 16 and the vicinity of the detection lens 1. As to the material of the lens 16, a material such as glass is employed because in a glass lens the birefringence inside thereof can be sufficiently removed.

Furthermore, for the $\lambda/4$-plate 14 and the polarization plate 15, stepping motors 17 and 18 and the gear systems thereof 19 and 20 for respectively rotating the $\lambda/4$-plate 14 and the polarization plate 15 around the light advancing direction are provided as a rotation medium 21. Sensors (not shown) for sensing the position of the rotation origin are respectively mounted on the stepping motors 17 and 18. Those sensors respectively count the number of pulses of the stepping motors 17 and 18. Thereby, the respective rotation angles of the $\lambda/4$-plate 14 and the polarization plate 15 can be detected. In practice, the respective rotation angles of the $\lambda/4$-plate 14 and the polarization plate 15 can be detected by the rotation angle detecting medium on the basis of the operation of counting the number of the pulses supplied to the stepping motors 17 and 18 in a personal computer 23, as mentioned below. The reference numeral 22 represents a motor driver for driving the stepping motors 17 and 18. The motor driver 22 receives the pulses from the personal computer 23 and the pulse generator 24 and drives the stepping motors respectively.

Furthermore, the image data photographed by the CCD camera 12 are taken into the memory of the personal computer 23 through an image inputting unit 25. And then, the birefringence phase difference of the detection lens 1 and the compass direction of the main axis is calculated by a predetermined method of operational calculation on the basis of the rotation angle data of the image data and data from positions of the stepping motors 17 and 18.

In such a way, the function of the operational calculation medium for calculating the birefringence of the detection lens 1 is practiced by the operational calculation processing function performed by the computer unit represented by the CPU included in the personal computer 23. In this connection, the image photographed by the CCD camera 12 is displayed on the monitor of the personal computer 23 or on another specially-used monitor.

Regarding such a structure as mentioned heretofore, the setting state of the birefringence measuring apparatus in the case of the first embodiment is described hereinafter.

At first, the compass direction of the polarization plate 7 against the surface of the ground is set to the horizontal direction, and that of the $\lambda/4$-plate 8 is set to a direction 45° inclined against the ground, namely, the setting is done so as to enable radiating the circular polarization light onto the detection lens 1.

Before performing the measurement, the compass direction of the $\lambda/4$-plate 14 is set so as to incline by 45° from the horizontal surface of the ground. In this state, in which the detection lens 1 is not yet set, the compass direction of the polarization plate 15 is rotated and at the same time the angle of the compass direction of the polarization plate 15 is set such that the intensity of the transmission light transmitted from the polarization plate 15 is minimized, namely, the transmission light transmitted therefrom becomes darkest. The compass direction angle is memorized in the memory as the rotation origin in the measurement.

On this occasion, it may also be allowed that, usually, a glass lens scarcely having any birefringence is tentatively set on the position of the detection lens 1 and the light rays directed to the polarization plate 15 and the CCD camera 12 as incident light are collimated. Regarding the distance between the lens 9 and the detection lens 1, for instance, the state in which the lens 9 and the detection lens 1 physically come closest to each other is set to a movement origin, and the stage 11 is moved from this movement origin. In this way, the distance between the lens 9 and the detection lens 1 can be detected.

Figure 18:
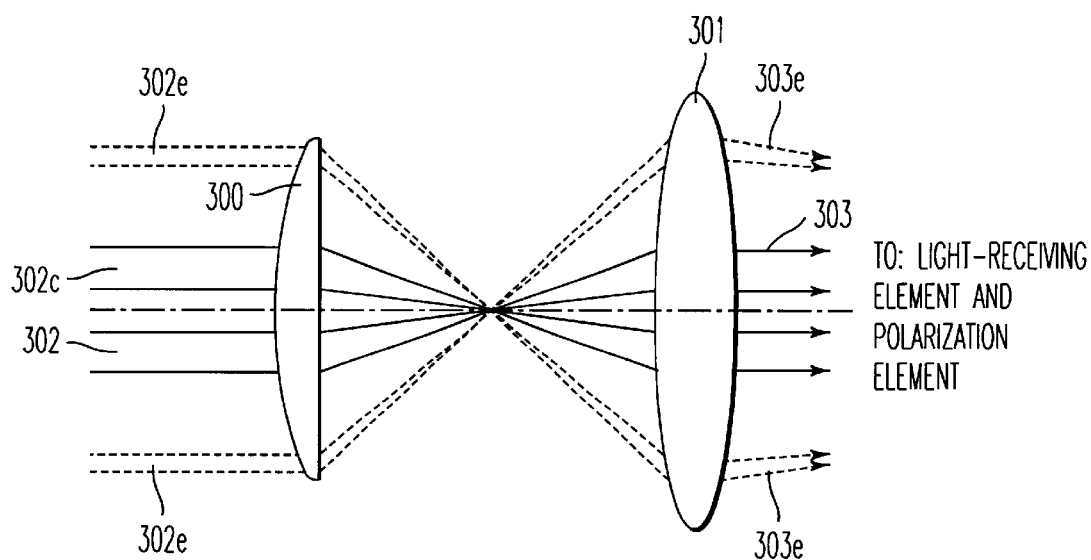
FIG. 18 is a structural view illustrating a structure of an optical system for explaining a defect of a background art measurement system.
Figure 19:
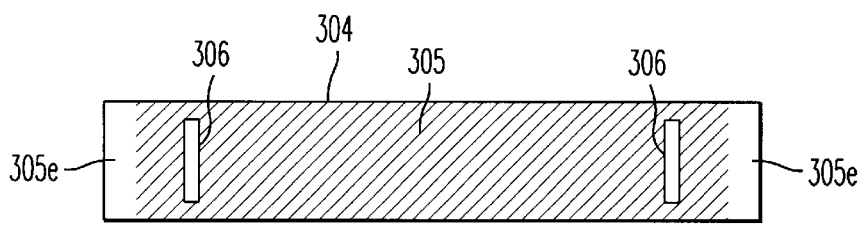
FIG. 19 is an explanatory diagram showing a state of a corresponding optical elasticity interference stripes.
Figure 20:
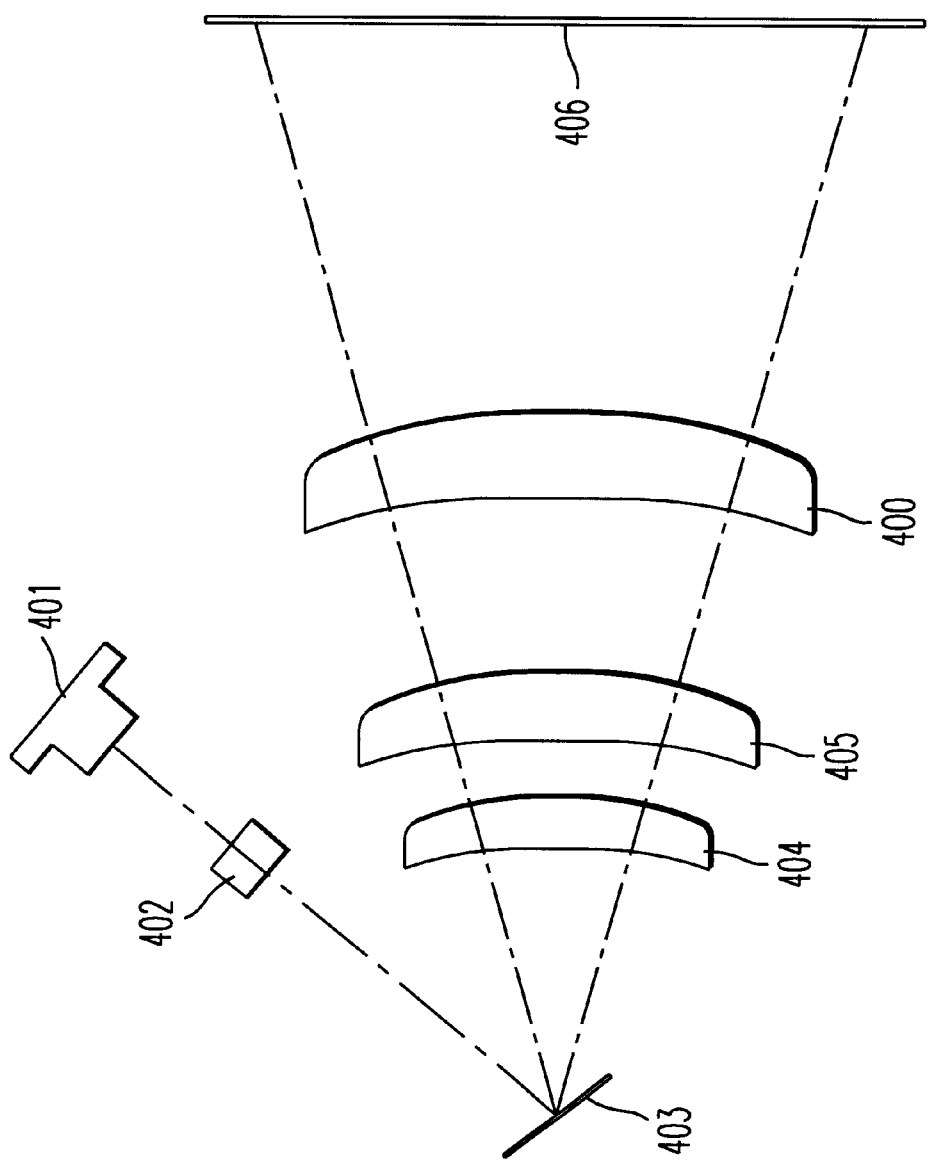
FIG. 20 is a plan view showing an outlined structural example of an optical system for writing-in light.

The first embodiment shows a measurement example of a state in which the focal point of the lens 9 is almost approximated to that of the detection lens 3. In such a state, the transmission light transmitted through the detection lens 1 usually becomes substantially parallel light. However, as illustrated in FIG. 18, the light rays from the circumferential edge of the detection lens 1 are observed as superposed light, or the transmission image of the detection lens is observed as distorted light. On such occasions, observing the transmission image of the detection lens 1, the distance between the lens 9 and the detection lens 1 is adjusted, and thereby the superposing of the light rays can be eliminated.

Figure 2:
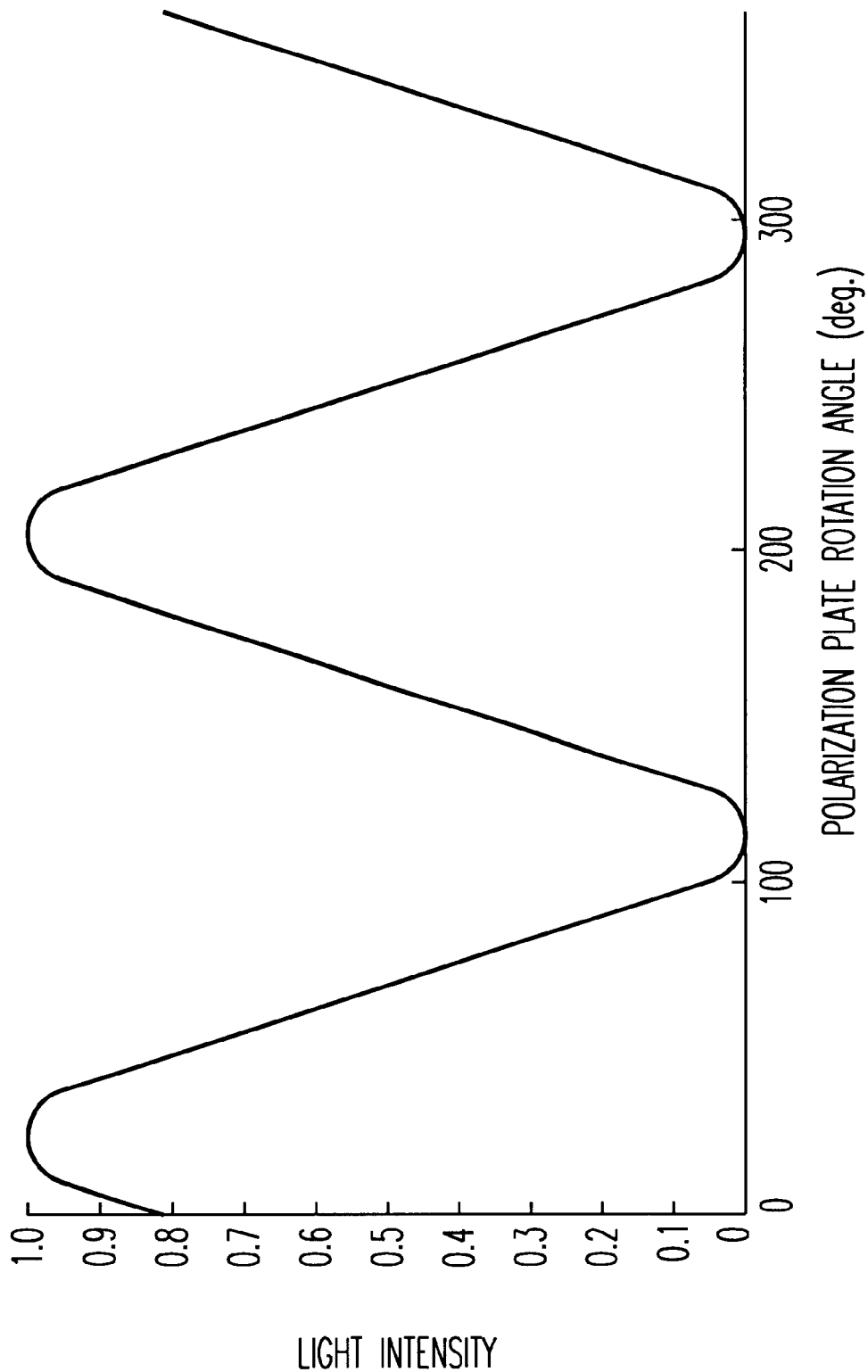
FIG. 2 is a property diagram for illustrating a property of rotation angle vs. light intensity.

Furthermore, regarding the writing-in optical system, assuming that the position on which the light rays are reflected is the focal point position of the lens 9 in FIG. 1, when the lens 9 and the detection lens 1 are set at the position of the distance corresponding to the distance between the scanning mirror surface in the writing-in optical system and the detection lens, it turns out to be possible to perform the measurement in a state closer to that of practical use of the light rays in the detection lens 1 in regard to the transmission.

Furthermore, in a case that the writing-in optical system is constructed with a plurality of lenses, the state of measurement approaches further closer to that of practical use. Consequently, it may be allowable to dispose another lens or lenses constructing the writing-in optical system on the optical axis.

In the practical measurement, at first the detection lens 1 is held with a holder and set at a predetermined position. The polarization plate 15 is rotated from the position of the rotation origin by every $(180/n)°$ in the state that the compass direction of the $\lambda/4$-plate 14 is at the inclination of 45°. The symbol "n" represent the number of the previously set measurement points.

Here, each time the polarization plate 15 is rotated by $(180/n)°$, the CCD image data read out by the CCD camera 12 are taken into the memory of the personal computer 23. Thereby, the rotation angle data of the polarization plate 15 and n sheets of the CCD image data can be acquired.

Next, the compass direction of the $\lambda/4$-plate 14 is set to 0° against the horizontal surface of the ground, and as in the aforementioned case, rotating the polarization plate 15 by every $(180/n)°$ from the position of the rotation origin, the CCD image data are taken into the memory of the personal computer 23, and thereby the rotation angle data of the polarization plate 15 and n sheets of the CCD image data can be acquired. In this way, the birefringence of the detection lens 1 can be obtained by performing the operational calculation process according to the following procedure by use of the operational calculation medium, on the basis of 2n sheets of the CCD image data and the rotation angle data of the polarization plate 15.

Now, the situation of the polarization state variation of the optical system in the measurement apparatus shown in FIG. 1 is represented by use of the Mueller matrix. Assuming that the Mueller matrix of the circular polarization light directed to the detection lens 1 as the incident light is L, the Mueller matrix of the detection lens 1 is T, the Mueller matrix of the λ/4-plate 14 is Q, and the Mueller matrix of the polarization plate 15 is A, Stokes' meter S can be obtained from the above factors and others.

At first, the Stokes' parameter S45 at the time of setting the azimuth of the 80 /4-plate 14 is set to the angle of 45° against the horizontal direction on the ground surface as $S_{45}=A\cdot Q_{45}\cdot T\cdot L$ $$S_{45} = A \cdot Q_{45} \cdot T \cdot L = \quad (1)$$

$$\frac{1}{2}\begin{pmatrix} 1 & \cos2\theta & \sin2\theta & 0 \\ \cos2\theta & \cos^2 2\theta & \sin2\theta\cos2\theta & 0 \\ \sin2\theta & \sin2\theta\cos2\theta & \sin^2 2\theta & 0 \\ 0 & 0 & 0 & 0 \end{pmatrix}\begin{pmatrix} 1 & 0 & 0 & 0 \\ 0 & 0 & 0 & -1 \\ 0 & 0 & 1 & 0 \\ 0 & 1 & 0 & 0 \end{pmatrix}\downarrow\rightarrow$$

$$\begin{pmatrix} 1 & 0 & 0 & 0 \\ 0 & 1-(1-\cos\delta)\sin^2\phi & (1-\cos\delta)\sin2\phi\cos2\phi & -\sin\delta\sin2\phi \\ 0 & (1-\cos\delta)\sin2\phi\cos2\phi & 1-(1-\cos\delta)\cos^2\phi & \sin\delta\cos2\phi \\ 0 & \sin\delta\sin2\phi & -\sin\delta\cos2\phi & \cos\delta \end{pmatrix}$$

$$\begin{pmatrix} 1 \\ 0 \\ 0 \\ -1 \end{pmatrix} = \frac{1}{2}\begin{pmatrix} 1+\cos\delta\cos2\theta-\sin\delta\cos2\phi\sin2\theta \\ \cos2\theta+\cos\delta\cos^2 2\theta-\sin\delta\cos2\phi\sin2\theta\cos2\theta \\ \sin2\theta+\cos\delta\sin2\theta\cos2\theta-\sin\delta\cos2\phi\sin^2\theta \\ 0 \end{pmatrix}$$

From the equation (1), the light intensity 145 obtained on the CCD camera 12 can be calculated in accordance with the equation (2).

$$I_{45} = \frac{1}{2}(1 + \cos\delta\cos2\theta - \sin\delta\cos2\phi\sin2\theta) \quad (2)$$

In the equations (1) and (2), θ is the main axis azimuth of the polarization plate 15, δ is the birefringence phase difference of the detection lens 1, and φ is the main axis azimuth of the detection lens 1.

When the polarization plate 15 is rotated by the stepping motor 18, the value of θ in the equations (1) and (2) is changed, and the light intensity I45 in the equation (2) obtained by the CCD camera 12 is also changed. FIG. 2 shows the situation of the variation of the light intensity I45 in accordance with the rotation of the main axis azimuth of the polarization plate 15. However, the value of the longitudinal axis light intensity I45 has been already normalized with the maximum value "1" and the minimum value "0".

Here, assuming that the resolution performance in the rotation angle reading-out operation of the polarization plate 15 is R (rotation angle corresponding to one pulse of the stepping motor 18), the phase φ45 of the light intensity variation in accordance with the rotation of the main axis compass direction of the polarization plate 15 can be obtained by the equation (3) on the basis of the actually-measured CCD image date and the rotation angle date of the polarization plate 15.

$$\phi_{45} = \tan^{-1}\left\{\frac{2R\sum(I_{45i}\cdot\sin\theta_i)}{2R\sum(I_{45i}\cdot\cos\theta_i)}\right\} \quad (3)$$

Next, the Stokes' parameter S0 at the time of setting the compass direction of the λ/4-plate 14 to 0° with respect to the direction of the horizontal surface of the ground can be represented by the equation (4).

$$S_0 = A \cdot Q_0 \cdot T \cdot L = \quad (4)$$

$$\frac{1}{2}\begin{pmatrix} 1 & \cos2\theta & \sin2\theta & 0 \\ \cos2\theta & \cos^2 2\theta & \sin2\theta\cos2\theta & 0 \\ \sin2\theta & \sin2\theta\cos2\theta & \sin^2 2\theta & 0 \\ 0 & 0 & 0 & 0 \end{pmatrix}\begin{pmatrix} 1 & 0 & 0 & 0 \\ 0 & 1 & 0 & 0 \\ 0 & 0 & 0 & 1 \\ 0 & 0 & -1 & 0 \end{pmatrix}\downarrow\rightarrow$$

$$\begin{pmatrix} 1 & 0 & 0 & 0 \\ 0 & 1-(1-\cos\delta)\sin^2\phi & (1-\cos\delta)\sin2\phi\cos2\phi & -\sin\delta\sin2\phi \\ 0 & (1-\cos\delta)\sin2\phi\cos2\phi & 1-(1-\cos\delta)\cos^2\phi & \sin\delta\cos2\phi \\ 0 & \sin\delta\sin2\phi & -\sin\delta\cos2\theta & \cos\delta \end{pmatrix}$$

$$\begin{pmatrix} 1 \\ 0 \\ 0 \\ -1 \end{pmatrix} = \frac{1}{2}\begin{pmatrix} 1+\sin\delta\sin2\phi\cos2\theta-\cos\delta\sin2\theta \\ \cos2\theta+\sin\delta\sin2\theta\cos^2 2\theta-\cos\delta\sin2\theta\cos2\theta \\ \sin2theta+\sin\delta\sin2\phi\sin2\theta\cos2\theta-\cos\delta\sin^2\theta \\ 0 \end{pmatrix}$$

From the equation (4), the light intensity I0 obtained on the CCD camera 12 is represented by the equation (5).

$$I_0 = \frac{1}{2}(1 + \sin\delta\sin2\phi\cos2\theta - \cos\delta\sin2\theta) \quad (5)$$

In the equations (4) and (5), θ is the main axis azimuth of the polarization plate 15, δ is the birefringence phase difference of the detection lens 1, and φ is the main axis compass direction of the detection lens 1.

The phase φ0 of the light intensity variation in accordance with the rotation of the main axis compass direction of the polarization plate 15 can be obtained by the equation (6), as in the case of the equation (3).

$$\phi_0 = \tan^{-1}\left\{\frac{2R\sum(I_{0i}\cdot\sin\theta_1)}{2R\sum(I_{0i}\cdot\cos\theta_1)}\right\} \quad (6)$$

Changing the equations (2) and (5), the phases φ45 and φ0 are obtained by the following equations (7) and (8).

$$\phi_{45} = \tan^{-1}(\tan\delta\cos2\phi) \quad (7)$$

$$\phi_0 = \tan^{-1}\left(\frac{1}{\tan\delta\sin2\theta}\right) \quad (8)$$

Consequently, from the equations (3), (6), (7), and (8), the phrase difference δ and the main axis compass direction can be obtained by the following equations (9) and (10).

$$\delta = \tan^{-1}\sqrt{\tan^2\phi_{45} + \frac{1}{\tan^2\phi_0}} \quad (9)$$

$$\phi = \frac{1}{2}\tan^{-1}\left(\frac{1}{\tan\phi_0 \tan\phi_{45}}\right) \quad (10)$$

Consequently, according to the first embodiment, in the manner basically according to the rotative analyzer method, the transmission light transmitted through the detection lens 1 is directed to the polarization plate 15 for changing the polarization state as the incident light. Rotating the polarization plate 15, the light is received and detected by the CCD camera 12, and thereby the birefringence of the detection lens 1 is calculated. In such a situation, the distance between the lens 9 of the radiation optical system 2 for radiating the diffusion light onto the detection lens 1 and the detection lens can be optionally set. Observing the transmission image transmitted through the detection lens, the distance between the detection lens 1 and the lens 9 is adjusted. Thereby, it is possible to obtain optical elasticity interference fringes as a transmission image of the detection lens 1 which is at most slightly affected by optical distortion. Furthermore, the measurement of the birefringence can be precisely performed over the entire surface of the detection lens 1. At the same time, it is possible to easily cope with a change of the type of the detection lens 1. In such a way, a widely-usable apparatus for and method of measuring birefringence can be realized.

SECOND EMBODIMENT

A second embodiment of the present invention is described hereinafter, referring to FIG. 3 and FIG. 4 in which the same reference numerals are attached to the same portions as in A the first embodiment, and the descriptions thereof are omitted. The above is also true for the subsequent embodiments.

In the second embodiment, the λ/4-plate 14, the polarization plate 15, the lens 16, the CCD camera 12, and the rotation medium 21 are carried on a base 31. The base 31 can be moved along a guide 32 in a direction substantially perpendicular to the optical axis of the measurement optical system (up-and-down direction as shown by an arrow mark in FIG. 3). The base 31 is shiftedly driven by a stepping motor 33. Here, a light-receiving-side displacement medium 34 for moving and adjusting the unitary combination of the polarization plate 15, the lens 16, and the CCD camera 12 in the direction perpendicular to the optical axis is constructed with the base 31, the guide 32, and the stepping motor 33, etc.

Figure 3:
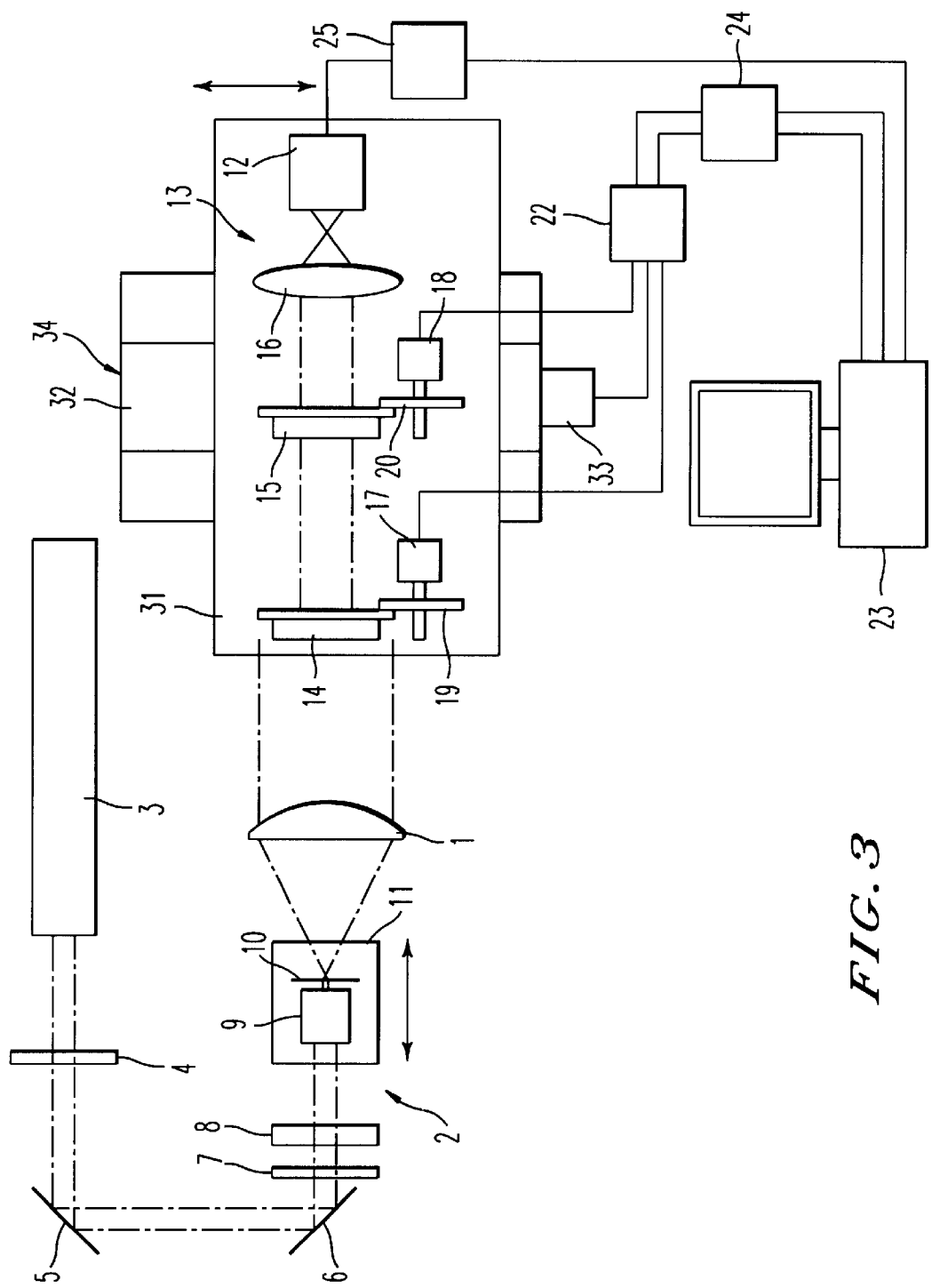
FIG. 3 is a structural view showing a second embodiment according to the present invention.

In the measurement optical system of such a structure as shown in FIG. 3, the vicinity of the detection lens 1 and the photographing surface of the CCD camera 12 is put in a focusing relationship by the action of the lens 36. For this reason, a spatial image of optical elasticity interference fringes created in the vicinity of the detection lens 1 by the birefringence of the detection lens 1 is photographed by the CCD camera 12 through the polarization plate 15. However, since the diffusion light radiated on the detection lens 1 is substantially collimated by the detection lens 1, the size (square measure) of the spatial image with optical elasticity interference fringes created in the vicinity of the detection lens 1 turns out to be almost the same as that of the detection lens 1.

On the other hand, the sizes (square measures) of the λ/4-plate 14 and the polarization plate 15 are almost 50 mm in diameter at a maximum, and it is impossible to cause the spatial image of the optical elasticity interference stripes of the size exceeding the above size to transmit once therethrough. As a result, when the diameter of the detection lens 1 becomes large, the measurement of the birefringence cannot be performed over the entire surface of the detection lens 1.

Regarding the above-mentioned points, it may be allowed that the size of the spatial image of the optical elasticity interference fringes is reduced once, and thereafter the spatial image is caused to transmit through the polarization plate 15. However, on this occasion, since the measurement optical system becomes complicated, and in addition the spatial image of the optical elasticity interference fringes becomes small, the spatial resolution in the measurement is lowered. In a case that the birefringence of the detection lens 1 is large, the distance between the optical elasticity interference fringes becomes narrower than the size of the CCD camera 12, and thereby the measurement itself may become impossible on some occasions.

For this reason, in the second embodiment, the optical system elements subsequent to the λ/4-plate 14 are combined unitarily and moved in a direction substantially perpendicular to the optical axis of the optical system. And then, the spatial image of the optical elasticity interference fringes having almost a same size as that of the detection lens 1 is partially divided into some pieces, and the image thus divided is observed by the CCD camera 12. In this way, the measurement is performed.

Figure 4:
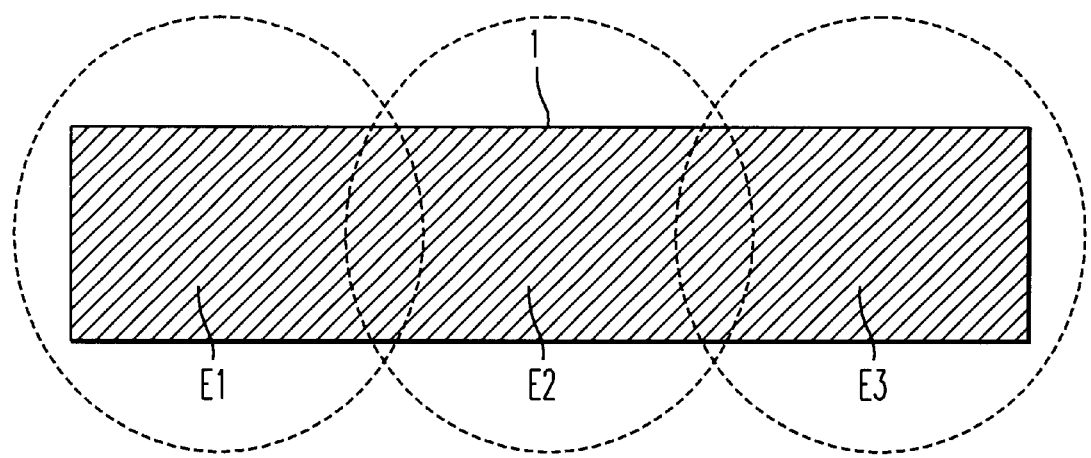
FIG. 4 is a front view showing a state of dividing an area to be measured.

For instance, as shown in FIG. 4, at first the base 31 is moved by the stepping motor 33 to enable observing the measured area E1 of the detection lens 1. In such a state, the phase difference and the main axis azimuth are measured in such a way as described in the first embodiment.

Following this step, the base 31 is moved by the stepping motor 33 to enable observing the measured area E2 of the detection lens 1. In such a state, the phase difference and the main axis azimuth are measured in the same manner, and further the base 31 is moved by the stepping motor 33 to enable observing the measured area E3 of the detection lens 1. In such a state, the phase difference and the main axis azimuth are measured in the same way.

Moreover, in the second embodiment, when the measured area of the detection lens 1 is determined, for instance, moving the base 31, the optical elasticity interference fringes are photographed and monitored by the CCD camera 12. Thereby, it may be allowed to select the suitable area. Or otherwise, it may also be allowed that a rotation origin position sensor is mounted on the stepping motor 33, and in such a structure, the movement distance of the base 31 can be detected by the number of pulses supplied to the stepping motor 33, and the measured area is previously decided and the base 31 is automatically moved onto the position on which the area can be observed.

Regarding the latter case, in practice, the movement distance of the base 31 (consequently, the polarization plate 15, etc.) is detected by the distance detecting medium on the basis of the operation of counting the number of the pulses supplied to the stepping motor 33 in the personal computer 23.

In such a way, according to the second embodiment, the measurement of the birefringence over the entire surface of the detection lens 1 can be performed without lowering the resolution.

THIRD EMBODIMENT

Figure 5:
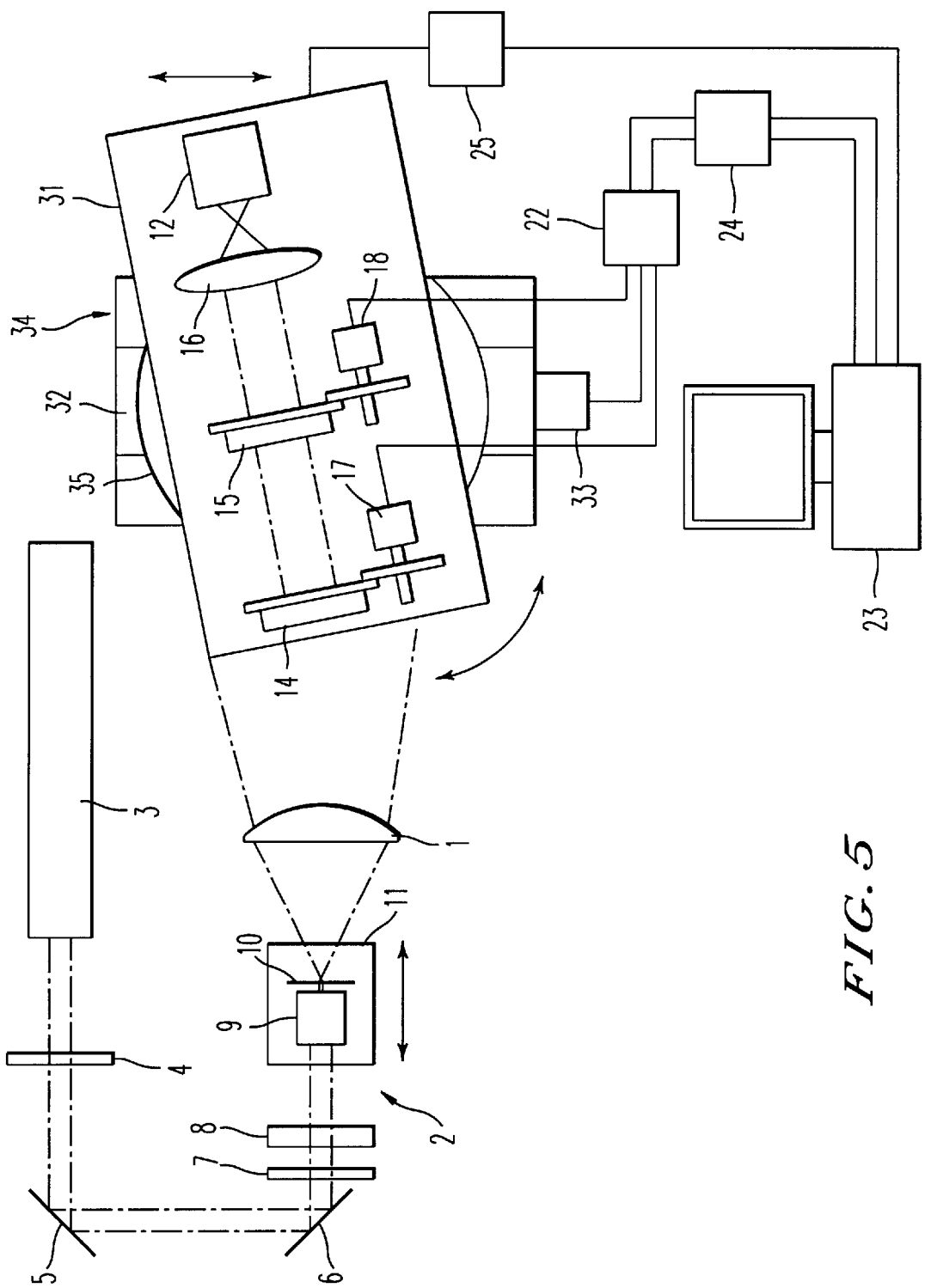
FIG. 5 is a structural view showing a third embodiment according to the present invention.

A third embodiment of the present invention is described hereinafter, referring to FIG. 5. In the third embodiment, the base 31 carrying the polarization plate 15 and the lens 16, etc. thereon is further carried and mounted on the rotative stage 35 serving as an angle changing medium. In such a structure, the angle of the polarization plate 15, etc. is changed from the advancing direction of the transmission light from the detection lens 1. Furthermore, there is provided an angle detecting medium for detecting an angle of the polarization plate 15, etc., although it is not shown in FIG. 5.

As mentioned before, in a case that the focal point of the lens 16 substantially coincides with that of the detection lens 1, since the transmission light of the detection lens 1 substantially coincides with the optical axis of the optical system over the entire surface of the detection lens 1, it is not necessary to rotate the direction of the $\lambda/4$-plate 14 or the polarization plate 15.

However, in a case that the detection lens 1 has a non-spherical surface, or in a case that the distance between the lens 9 and the detection lens 1 is changed to another value from the above-mentioned setting value (the setting value for substantially equalizing both of the focal distances), the light transmitted through the detection lens 1 does not become parallel with the optical axis of the optical system. As a result, the advancing angle of the light rays from the optical axis of the optical system turns out to differ in accordance with the measured area of the detection lens 1.

Furthermore, the $\lambda/4$-plate 14 and the polarization plate 15 have incident angle dependability for light rays. If the light rays are not directed vertically (perpendicularly) to the element surface, the predetermined function cannot be performed, and that results in one reason of measurement error occurrence.

Here, in the third embodiment, the $\lambda/4$-plate 14, the polarization plate 15, the lens 16, and the CCD camera 12 are unitarily rotated by the rotative stage 35 in such a situation. Thereby, the optical elements are opposed to the transmission light transmitted through the detection lens 1.

To state the operation more strictly in this connection, even in the partial measurement area capable of observing once, the advancing angle of the light rays differs to some extent in accordance with the place. However, the rotative stage 35 is rotated such that the element surface of the polarization plate 15 may become vertical (perpendicular or opposed) to the average advancing direction of the light rays from the optical axis of the optical system. Thereby, it is possible to perform the measurement with a small error occurrence. Furthermore, as to the advancing angle of the light rays from the optical axis of the optical system, for instance, since the angle is previously obtained every lens height of the detection lens 1 after passing through the detection lens 1 utilizing the light pursuing simulation, it is preferable to obtain the advancing angle of the average light rays in a partial area to be measured on the basis of the shape of the detection lens 1 or the setting of the measurement optical system. Furthermore, in the case of employing detection lenses respectively having different curvatures in the main scanning direction and in the subscanning direction, it is also preferable to further provide a flapping mechanism on the base 31 in addition to the rotation mechanism such as the rotation stage 35 and to three-dimensionally perform the same operation as mentioned above.

Consequently, according to the third embodiment, even in the case of utilizing a scanning lens in which the detection lens 1 is employed for light writing-in, basically, the measurement system can be set to a state of actual use utilizing a structure capable of optionally setting the distance between the detection lens 1 and the lens 9. In addition, the angle of the unitary combination of the polarization plate 15, etc. with respect to the advancing direction of the transmission light transmitted through the detection lens 1 is adjusted, and thereby the light can be directed almost vertically as the incident light. In such a structure, further precise measurements can be performed.

FOURTH EMBODIMENT

Figure 6:
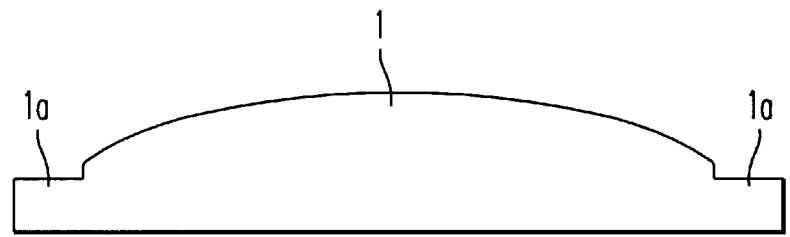
FIG. 6 is a side view showing an example of a shape of a detection lens in a fourth embodiment according to the present invention.
Figure 7:
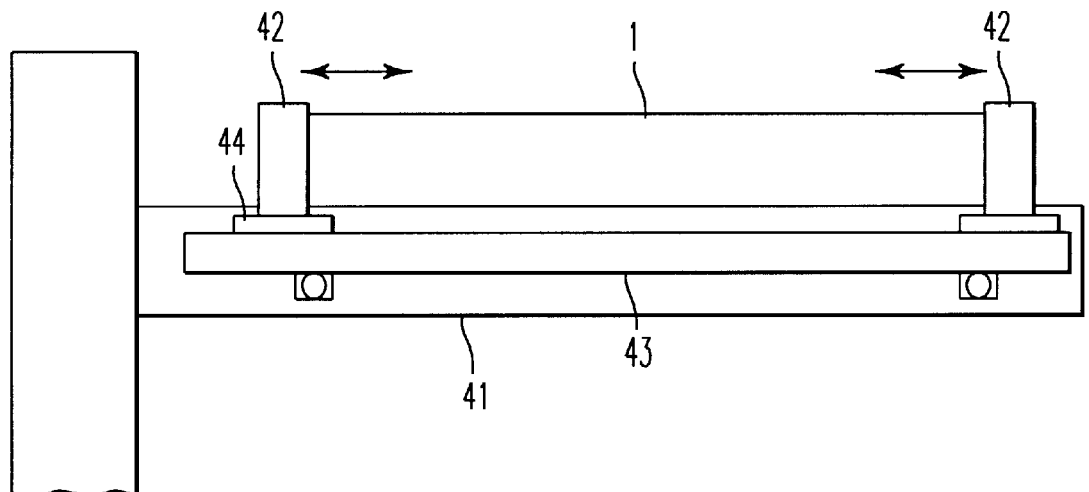
FIG. 7 is a structural view showing a light intercepting structure according to the present invention.

A fourth embodiment of the present invention is described hereinafter, referring to FIGS. 6 and 7. In the fourth embodiment, it is assumed that a lens of large diameter or another lens having a flat portion 1a on a circumferential edge portion thereof is employed as the detection lens 1 used in the aforementioned respective embodiments.

Under such an assumption as mentioned above, in the fourth embodiment, a light intercepting member 42 for intercepting transmission light transmitted through the circumferential edge portion of the detection lens 1 is provided in a holder 41 for holding the detection lens 1. The light intercepting member 42 is movably carried on a stage 44 serving as a light intercepting member moving medium so as to slide along the guide 43 of the holder 41. The position of the light intercepting member 42 from the detection lens 1 can be adjusted in a direction perpendicular to the optical axis.

In such a structure, in the case of employing a detection lens 1 of large diameter or a detection lens having a flat portion on the circumferential edge portion thereof, the transmission light rays from the circumferential edge portion of the detection lens 1 are superposed, or directed toward the side of the measurement system as stray light. As a result, the measurement is disturbed on some occasions. Regarding this point, in the fourth embodiment, since the light intercepting member 42 is provided on such a circumferential edge portion of the detection lens 1, and the transmission light transmitted through the circumferential edge portion is intercepted by the light intercepting member 42, there is no unpreferable influence due to the light disturbing the measurement. Generally, there exits an ineffective area of the lens on many occasions on such an area emitting the stray light from the flat portion 1a of the detection lens 1, etc., and therefore the measurement is not necessary on many occasions. In such a situation, by providing the light intercepting member 42 on such a portion, the essential measurement is not disturbed at all.

In the case of intercepting such light disturbing the measurement, monitoring the spatial image of the optical elasticity interference fringes, the stage 44 carrying the light intercepting member 42 is moved in a direction substantially perpendicular to the optical axis of the optical system (direction by the arrow mark in FIG. 7), and the position of the stage 44 is searched to eliminate influences due to stray light as a preferable method. On this occasion, the monitored image can be observed by the CCD camera 12, or such an image can be projected on a comparatively simple screen.

Consequently, according to the fourth embodiment, when the transmission light transmitted through the circumferential edge portion of the detection lens 1 is directed to the CCD camera 12 as incident light, the measurement is disturbed on some occasions. However, since the light intercepting member 42 is provided on the circumferential edge portion of the detection lens 1, there is no unpreferable influence due to stray light, and it is possible to eliminate the area where the measurement cannot be performed. Thereby, the measurement can be performed over the entire surface of the detection lens 1. In particular, by suitably moving the light intercepting member 42 by use of the stage 44, the influence due to the stray light can be completely removed for the detection lens 1.

In the birefringence measuring apparatus and method of the invention as a feature, in a manner basically according to the rotative analyzer method, the transmission light transmitted through the detection lens is directed to the polarization element for changing the polarization state as the incident light. Rotating the polarization element, the light is received and detected by the array state light-receiving element, and thereby the birefringence of the detection lens is calculated. In such a situation, the distance between the radiation optical system for radiating the diffusion light onto the detection lens and the detection lens can be optionally set. Observing the transmission image transmitted through the detection lens, the distance between the detection lens and the radiation optical system is adjusted. Thereby, it is possible to obtain optical elasticity interference fringes of the transmission image of the detection lens 1 which at most are only slightly affected by optical distortion. Furthermore, the measurement of the birefringence can be precisely performed over the entire surface of the detection lens 1. At the same time, it is possible to easily cope with a change of a type of the detection lens. In such a way, a widely-usable apparatus for and method of measuring the birefringence can be realized.

In the birefringence measuring apparatus and method of the invention as a further feature, if the polarization element, the focusing optical system, and the light-receiving element are combined into a unitary (integrated) unit and moved in a direction substantially perpendicular to the optical axis, that is, a longitudinal direction of the detection lens, and thereby, dividing the unitary combination of those elements, the birefringence thereof can be measured, and the measurement of the birefringence of the entire detection lens can be realized with low cost without lowering resolution thereof.

In the birefringence measuring apparatus and method of the invention as a further feature, even in a case in which the detection lens is employed for writing-in light, the measurement system can be set to a state near practical use of the detection lens by use of a structure capable of optionally set the distance between the detection lens and the radiation optical system. In addition, by adjusting an angle of the unitary combination of the polarization element, etc. with respect to the advancing direction of the transmission light transmitted through the detection lens, the light can be directed almost vertically as incident light, and the measurement of the birefringence thereof can be further precisely performed.

In the birefringence measuring apparatus and method of the invention as a further feature, when the transmission light transmitted through the circumferential edge portion of the detection lens is directed to a light-receiving element as incident stray light, the measurement of the birefringence is disturbed. However, if a light intercepting member is provided on such a circumferential edge portion thereof, the unfavorable influence due to the stray light as mentioned above can be eliminated, and thereby the area in which the birefringence cannot be measured can be eliminated. Consequently, by suitably moving the light intercepting member by use of a light intercepting member moving medium, the unfavorable influence due to the stray light for the detection lens can be removed.

FIFTH EMBODIMENT

Figure 8:
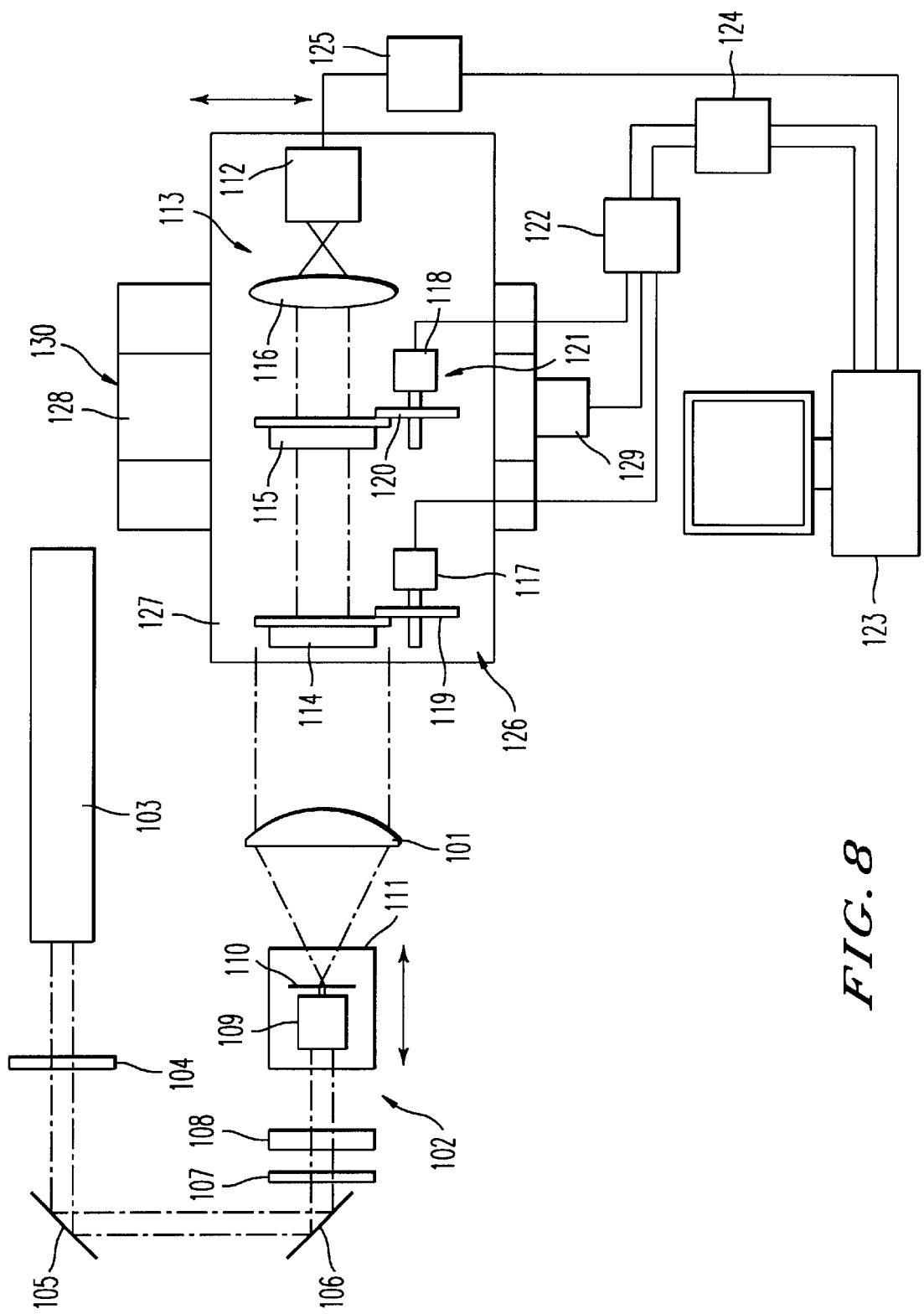
FIG. 8 is a structural view showing a fifth embodiment according to the present invention.

A fifth embodiment of the present invention is described hereinafter, referring to FIGS. 2, 4, 8, and 9. In FIG. 8, the detection lens 101 as an object to be measured in the fifth embodiment is held by a holder (not shown). At first, a radiation optical system 102 for radiating the light onto the detection lens 101 in a state of a predetermined polarization is provided for such detection lens 101.

The above-mentioned radiation optical system 102 is constructed with a He—Ne laser 103 employed as a light source for emitting a light beam of random polarization, an ND filter 104 for adjusting the light intensity, deflection mirrors 105 and 106, a polarization plate 107 for converting the light from the He—Ne laser 103 to a straight-line polarization light, a $\lambda/4$-plate 108 for further converting the straight-line polarization light converted by the polarization plate 107 to a circular polarization light, a lens 109, and a pin hole 110.

The lens 109 equally serves as the object lens of a microscope and radiates the diffusion light toward the detection lens 101. The pin hole 110 functions as a spatial filter. The lens 109 and the pin hole 110 are carried on a stage 111 capable of moving in the optical axis direction. The lens 109 and the pin hole 110 are moved back and forth in the optical axis direction by the rotative action of a stepping motor (not shown) for driving the stage 111.

Here, a radiation-side displacement medium is constructed with the stage 111, the stepping motor, etc., and the position of the lens 109 in the optical axis direction from the detection lens 101 can be adjusted. Furthermore, a position sensor for sensing a rotation origin (starting point) is provided on the stepping motor. The distance between the lens 109 and the detection lens 101 is previously set to a predetermined distance. Assuming that the position is determined from the movement origin of the stage 111, the variation of the distance between the lens 109 and the detection lens 101 caused by the movement of the stage 111 can be detected by counting the number of pulses supplied to the stepping motor. In practice, the distance can be detected on the basis of an operation of counting the pulses supplied to the stepping motor in the personal computer 123 as discussed below (by use of a distance detecting medium included therein).

Furthermore, a CCD camera 112 serving as an array-state light receiving element for receiving transmission light is provided on the optical axis at the transmission/emission side of the detection lens 101. A focusing optical system 113 is provided between the detection lens 101 and the CCD camera 112. The focusing optical system 113 is constructed with $\lambda/4$-plate 114 for converting light flux of elliptic polarization approximated to circular polarization to light flux of elliptic polarization approximated to straight-line polarization by the action of the birefringence at the time of passing through the detection lens 101, and a focusing lens 116 for focusing light passing through the polarization plate 115, serving as the polarization element, onto the CCD camera 112.

The lens 116 is a lens combination capable of changing its focal distance, and may be constructed of a plurality of lenses. By changing the distance between the lenses constructing the lens combination, the focal distance of the lens combination can be changed and the focusing magnification rate thereof can also be changed. If the position of the lens 116 is previously adjusted to establish the focusing relationship in the vicinity of the detection lens 101, the focusing magnification rate of the focusing optical system 113 can be changed on the condition of keeping the focusing relationship. As to the material of the lens 116, a material such as a glass lens in which the birefringence thereof is sufficiently removed can be used for the lens 116.

Furthermore, for the λ/4-plate 114 and the polarization plate 115, stepping motors 117 and 118 and the gear systems thereof 119 and 120 for respectively rotating the λ/4-plate 114 and the polarization plate 115 around the light advancing direction are provided for a rotation medium 121. Sensors (not shown) for sensing the position of the rotation origin are respectively mounted on the stepping motors 117 and 118. The sensors respectively count the number of the pulses of the stepping motors 117 and 118. Thereby, the respective rotation angles of the λ/4-plate 114 and the polarization plate 115 can be detected by the rotation angle detecting medium on the basis of an operation of counting the number of the pulses supplied to the stepping motors 117, 118 in the personal computer 123 as discussed below. The reference numeral 122 represents a motor driver for driving the stepping motors 117 and 118. The motor driver 122 receives the pulses from the personal computer 123 and the pulse generator 124, and drives the stepping motors 117 and 118 respectively.

Furthermore, the image data photographed by the CCD camera 112 are taken into the memory of the personal computer 123 through an image inputting unit 125. And then, the birefringence phase difference of the detection lens 101 and the azimuth of the main axis is calculated by the predetermined method of the operational calculation on the basis of the rotation angle data of the image data and the positions of the stepping motors 117 and 118.

In such a way, the function of the operational calculation medium for calculating the birefringence of the detection lens 101 is practiced by the operational calculation processing function performed by the computer unit represented by the CPU included in the personal computer 123. In this connection, the image photographed by the CCD camera 112 is displayed on the monitor of the personal computer 123 or on another specially-used monitor.

Furthermore, the unitary combination of the λ/4-plate 114, the polarization plate 115, the lens 116, the CCD camera 112, and the rotation medium 121 combined as the light receiving unit 126 is carried on the common base 127. The combination thus carried thereon can be moved along the guide 128 in a direction substantially perpendicular to the optical axis of the measurement optical system (in FIG. 1, up-and-down direction as shown by the arrow mark). The base 127 is driven to be displaced by stepping motor 129. Here, a light-receiving side displacement medium 130 for moving and adjusting the light-receiving unit 126 in the direction perpendicular to the optical axis is constructed with the base 127, the guide 128, and the stepping motor 129, etc.

In such a structure, it is first assumed that, in the measurement optical system shown in FIG. 8, the area around the detection lens 101 and the photographing surface of the CCD camera 112 is put in a focusing relationship by action of the lens 116. With such an assumption, the spatial image of the optical elasticity interference stripes occurring in the vicinity of the detection lens 101 by action of the birefringence of the lens 101 turns out to be photographed through the polarization plate 115 by the CCD camera 112. However, the diffusion light radiated onto the detection lens 101 is almost completely collimated by the detection lens 101, the size (square measure) of the spatial image of the optical elasticity interference stripes occurring in the vicinity of the detection lens 101 becomes almost the same as that of the detection lens 101.

On the other hand, the size (square measure) of the combination of the λ/4-plate 114 and the polarization plate 115 constructing the measurement optical system is almost 30 mm in diameter at a maximum, and therefore, it is impossible to cause the spatial image of the optical elasticity interference stripes of a size exceeding that of the above combination thereof to be transmitted once therethrough. As a result, when the diameter of the detection lens 101 becomes large, the measurement of the birefringence over the entire surface of the detection lens 101 becomes impossible.

Regarding this point, it may be allowable that the size of the optical elasticity interference fringes is reduced once, and thereafter, the light is transmitted through the λ/4-plate 114 and the polarization plate 115. However, on this occasion, the measurement optical system becomes complicated, and in addition, the spatial image of the optical elasticity interference fringes is also reduced, and thereby the spatial resolution is lowered in the measurement. Furthermore, in a case that the birefringence of the detection lens 101 is large, the distance between the optical elasticity interference fringes becomes narrower than the size of the CCD camera 112, and thereby, the measurement itself becomes impossible on some occasions.

For coping with such problems, in the present embodiment, the optical system elements subsequent to the λ/4-plate 114 are unitarily combined into a single unit as the light-receiving unit 126.

The light-receiving unit 126 thus combined is moved in the direction substantially perpendicular to the optical axis of the optical system, and the spatial image of the optical elasticity interference stripes having almost a same size as that of the detection lens 101 is partially divided into some portions, and the divided image is observed by use of the CCD camera 112. In this way, the measurement is performed.

For instance, as shown in FIG. 4, the base 127 is firstly moved by the stepping motor 129 to enable observing the measured area E1 of the detection lens 101. On such a condition as mentioned above, the phase difference and the azimuth of the main axis is measured in such a manner as discussed below.

Following these steps, the base 127 is moved by the stepping motor 129 to enable observing the measured area E2 of the detection lens 101. In such a state, the phase difference and the azimuth of the main axis are measured in the same way. The base 127 is further moved by the stepping motor 129 to enable observing the measured area E3 of the detection lens 101. In such a state, the phase difference and the azimuth of the main axis are measured in the same way.

Moreover, in the case of determining the measured area of the detection lens 101, for instance, by moving the base 127 and observing, at the same time, the optical elasticity interference fringes photographed and monitored by the CCD camera 112, the suitable area can be preferably selected. Or otherwise, a rotation origin position sensor is mounted on the stepping motor 129. The movement distance of the base 127 can be detected by the number of the pulses supplied to the stepping motor 129. In such a structure, it may be allowed that the measured area has been previously decided and the base 127 is automatically moved to the position on which the area can be observed.

On the latter occasion, the movement distance of the base 127 (namely, the polarization plate 115, etc.) is detected, in practice, by the distance detecting medium, on the basis of the operation of counting the number of the pulses supplied to the stepping motor 129 in the personal computer 123.

In such a way, according to the present embodiment, the birefringence of the entire detection lens 101 can be measured without lowering the resolution.

Regarding such a structure as mentioned heretofore, the setting state of the birefringence measuring apparatus in the case of the present embodiment is described hereinafter.

At first, the azimuth of the polarization plate 107 with respect to the surface of the ground is set to the horizontal direction, and that of the λ/4-plate 108 is set to a direction 45° inclined against the ground, namely, the setting is done to enable radiating the circular polarization light onto the detection lens 101.

Before performing the measurement, the azimuth of the λ/4-plate 114 is set to be inclined by 45° from the horizontal surface of the ground. In this state, in which the detection lens 101 is not yet set, the azimuth of the polarization plate 115 is rotated and at the same time the angle of the azimuth of the polarization plate 115 is set such that the intensity of the transmission light transmitted from the polarization plate 115 is minimized, namely, the transmission light transmitted therefrom becomes darkest. The azimuth angle is then memorized in the memory as the rotation origin of the measurement.

On this occasion, it may also be allowed that, usually, the glass lens scarcely having the birefringence is tentatively set on the position of the detection lens 101 and the light rays directed to the polarization plate 115 and the CCD camera 112 as incident light are collimated. Regarding the distance between the lens 109 and the detection lens 101, for instance, the state in which the lens 109 and the detection lens 101 physically come closest to each other is set as a movement origin, and the stage 111 is moved from this movement origin. In such a way, the distance between the lens 109 and the detection lens 101 can be detected.

The present embodiment shows the measurement example of the state in which the focal point of the lens 109 is almost approximated to that of the detection lens 101. In such a state, the transmission light transmitted through the detection lens 101 usually becomes almost parallel light. However, as illustrated in FIG. 18, the light rays from the circumferential edge of the detection lens 101 are observed as superposed light, or the transmission image of the detection lens is observed as distorted light. On such occasions, observing the transmission image of the detection lens 101, the distance between the lens 109 and the detection lens 101 is adjusted, and thereby the superposing of the light rays can be eliminated.

Furthermore, regarding the writing-in optical system, assuming that the position on which the light rays are reflected is the focal point position of the lens 109 in FIG. 8, when the lens 109 and the detection lens 101 are set at positions of a distance corresponding to the distance between a scanning mirror surface in the writing-in optical system and the detection lens, it turns out to be possible to perform the measurement in a state closer to that of the practical use of the light rays in the detection lens 101 in regard to the transmission.

Furthermore, in a case that the writing-in optical system is constructed with a plurality of lenses, the state of measurement is further closer to that of the practical use. Consequently, it may be allowable to dispose another lens or lenses constructing the writing-in optical system on the optical axis.

In the practical measurement, at first, the detection lens 101 is held with a holder and is set at a predetermined position. The polarization plate 115 is rotated from the position of the rotation origin by every (180/n)° in the state that the azimuth of the λ/4-plate 114 is at an inclination of 45°. The symbol "n" represents the number of the previously set measurement points.

Here, every time the polarization plate 115 is rotated by (180/n)°, the CCD image data read out by the CCD camera 112 is taken into the memory of the personal computer 123. Thereby, the rotation angle data of the polarization plate 115 and n sheets of the CCD image data can be acquired.

Next, the azimuth of the λ/4-plate 114 is set to 0° with respect to the horizontal surface the ground, and as in the aforementioned case, rotating the polarization plate 115 by every 180/n)° from the position of the rotation origin, the CCD image data are taken into the memory of the personal computer 123, and thereby the rotation angle data of the planarization plate 115 and n sheets of the CCD image data can be acquired. In such a way, the birefringence of the detection lens 101 can be obtained by performing the operational calculation process according to the following procedure, on the basis of 2n sheets of the CCD image data and the rotation angle data of the polarization plate 115 acquired by the personal computer 123.

At first, the Stokes' parameter S45 at the time of setting the azimuth of the λ/4-plate 114 is set to the angle of 45° with respect to the horizontal direction on the ground surface.

$$S_{45} = A \cdot Q_{45} \cdot T \cdot L = \qquad (11)$$

$$\frac{1}{2}\begin{pmatrix} 1 & \cos2\theta & \sin2\theta & 0 \\ \cos2\theta & \cos^2 2\theta & \sin2\theta\cos2\theta & 0 \\ \sin2\theta & \sin2\theta\cos2\theta & \sin^2 2\theta & 0 \\ 0 & 0 & 0 & 0 \end{pmatrix} \begin{pmatrix} 1 & 0 & 0 & 0 \\ 0 & 0 & 0 & -1 \\ 0 & 0 & 1 & 0 \\ 0 & 1 & 0 & 0 \end{pmatrix} \downarrow \rightarrow$$

$$\begin{pmatrix} 1 & 0 & 0 & 0 \\ 0 & 1-(1-\cos\delta)\sin^2\phi & (1-\cos\delta)\sin2\phi\cos2\phi & -\sin\delta\sin2\phi \\ 0 & (1-\cos\delta)\sin2\phi\cos2\phi & 1-(1-\cos\delta)\cos^2\phi & \sin\delta\cos2\phi \\ 0 & \sin\delta\sin2\phi & -\sin\delta\cos2\phi & \cos\delta \end{pmatrix}$$

$$\begin{pmatrix} 1 \\ 0 \\ 0 \\ -1 \end{pmatrix} =$$

$$\frac{1}{2}\begin{pmatrix} 1 + \cos\delta\cos2\theta - \sin\delta\cos2\phi\sin2\theta \\ \cos2\theta + \cos\delta\cos^2 2\theta - \sin\delta\cos2\phi\sin2\theta\cos2\theta \\ \sin2\theta + \cos\delta\sin2\theta\cos2\theta - \sin\delta\cos2\phi\sin^2 2\theta \\ 0 \end{pmatrix}$$

From the equation (11), the light intensity $I_{45}$ obtained on the CCD camera 112 can be calculated in accordance with the equation (12).

$$I_{45} = \frac{1}{2}(1 + \cos\delta\cos2\theta - \sin\delta\cos2\phi\sin2\theta) \qquad (12)$$

In the equations (11) and (12), θ is the main axis compass direction of the polarization plate 115, δ is the birefringence phase difference of the detection lens 101, and φ is the main axis compass direction of the detection lens 101.

When the polarization plate 115 is rotated by the stepping motor 118, the value of θ in the equations (11) and (12) is changed, and the light intensity $I_{45}$ in the equation (12) obtained by the CCD camera 112 is also changed. FIG. 2 shows the situation of the variation of the light intensity $I_{45}$ in accordance with the rotation of the main axis compass direction of the polarization plate 115. However, the value of the longitudinal axis light intensity $I_{45}$ has been already normalized with the maximum value "1" and the minimum value "0".

Here, assuming that the resolution ability in the rotation angle reading-out operation of the polarization plate 115 is R (rotation angle corresponding to one pulse of the stepping motor 118), the phase φ45 of the light intensity variation in accordance with the rotation of the main axis compass direction of the polarization plate 115 can be obtained by the equation (13) on the basis of the actually-measured CCD image data and the rotation angle data of the polarization plate 115.

$$\phi_{45} = \tan^{-1}\left\{\frac{2R\sum(I_{45i}\cdot\sin\theta_i)}{2R\sum(I_{45i}\cdot\cos\theta_i)}\right\} \quad (13)$$

Next, the Stokes' parameter $S_0$ at the time of setting the azimuth of the λ/4-plate 114 to 0° with respect to the direction of the horizontal surface of the ground can be represented by the equation (14), $$S_0 = A \cdot Q_0 \cdot T \cdot L =$$

$$\frac{1}{2}\begin{pmatrix} 1 & \cos2\theta & \sin2\theta & 0 \\ \cos2\theta & \cos^2 2\theta & \sin2\theta\cos2\theta & 0 \\ \sin2\theta & \sin2\theta\cos2\theta & \sin^2 2\theta & 0 \\ 0 & 0 & 0 & 0 \end{pmatrix}\begin{pmatrix} 1 & 0 & 0 & 0 \\ 0 & 1 & 0 & 0 \\ 0 & 0 & 0 & 1 \\ 0 & 0 & -1 & 0 \end{pmatrix}\downarrow\rightarrow$$

$$\begin{pmatrix} 1 & 0 & 0 & 0 \\ 0 & 1-(1-\cos\delta)\sin^2\phi & (1-\cos\delta)\sin2\phi\cos2\phi & -\sin\delta\sin2\phi \\ 0 & (1-\cos\delta)\sin2\phi\cos2\phi & 1-(1-\cos\delta)\cos^2 2\phi & \sin\delta\cos2\phi \\ 0 & \sin\delta\sin2\phi & -\sin\delta\cos2\phi & \cos\delta \end{pmatrix}$$

$$\begin{pmatrix} 1 \\ 0 \\ 0 \\ -1 \end{pmatrix} =$$

$$\frac{1}{2}\begin{pmatrix} 1+\sin\delta\sin2\phi\cos2\theta-\cos\delta\sin2\theta \\ \cos2\theta+\sin\delta\sin^2 2\theta-\cos\delta\sin2\theta\cos2\theta \\ \sin2\theta+\sin\delta\sin2\phi\sin2\theta\cos2\theta-\cos\delta\sin^2\theta \\ 0 \end{pmatrix}$$

(14)

From the equation (14), the light intensity IO obtained on the CCD camera is represented by the equation (15)

$$I_0 = \frac{1}{2}(1+\sin\delta\sin2\phi\cos2\theta-\cos\delta\sin2\theta) \quad (15)$$

In the equations (14) and (15), θ is the main axis compass direction of the polarization plate 115, δ is the birefringence phase difference of the detection lens 101, and φ is the main axis azimuth of the detection lens 101.

The phase φ0 of the light intensity variation in accordance with the rotation of the main axis azimuth of the polarization plate 115 can be obtained by the equation (16), as in the case of the equation (13).

$$\phi_0 = \tan^{-1}\left\{\frac{2R\sum(I_{0i}\cdot\sin\theta_i)}{2R\sum(I_{0i}\cdot\cos\theta_i)}\right\} \quad (16)$$

Changing the equation (12) and (15), the phases φ45 and φ0 are obtained by the following equations (17) and (18).

$$\phi_{45} = \tan^{-1}(\tan\delta\cos2\phi) \quad (17)$$

$$\phi_0 = \tan^{-1}\left(\frac{1}{\tan\delta\sin2\theta}\right) \quad (18)$$

Consequently, from the equations (13), (16), (17), and (18), the phase difference δ and the main axis azimuth φ can be obtained by the following equations (13) and (20).

$$\delta = \tan^{-1}\sqrt{\tan^2\phi_{45}+\frac{1}{\tan^2\phi_0}} \quad (19)$$

$$\phi = \frac{1}{2}\tan^{-1}\left(\frac{1}{\tan\phi_0\tan\phi_{45}}\right) \quad (20)$$

Consequently, according to the present embodiment, in the manner basically according to the rotative analyzer method, the transmission light transmitted through the detection lens 101 is directed to the polarization plate 115 for changing the polarization state as the incident light. Rotating the polarization plate 115, the light is received and the birefringence of the detection lens 101 is calculated. In such a situation, the distance between the lens 109 of the radiation optical system 102 for radiating the diffusion light onto the detection lens 101 and the detection lens 101 can be optionally set. Observing the transmission image transmitted though the detection lens 101, the distance between the detection lens 101 and the lens 109 is adjusted. Thereby, it is possible to obtain the optical elasticity interference fringes of the transmission image of the detection lens 101 which at most are only slightly affected by optical distortion. Furthermore, the measurement of the birefringence can be precisely performed over the entire surface of the detection lens 101. At the same time, it is possible to easily cope with a change in the type of the detection lens 101. In such a way, a widely-usable apparatus for and method of measuring the birefringence can be realized.

Figure 9:
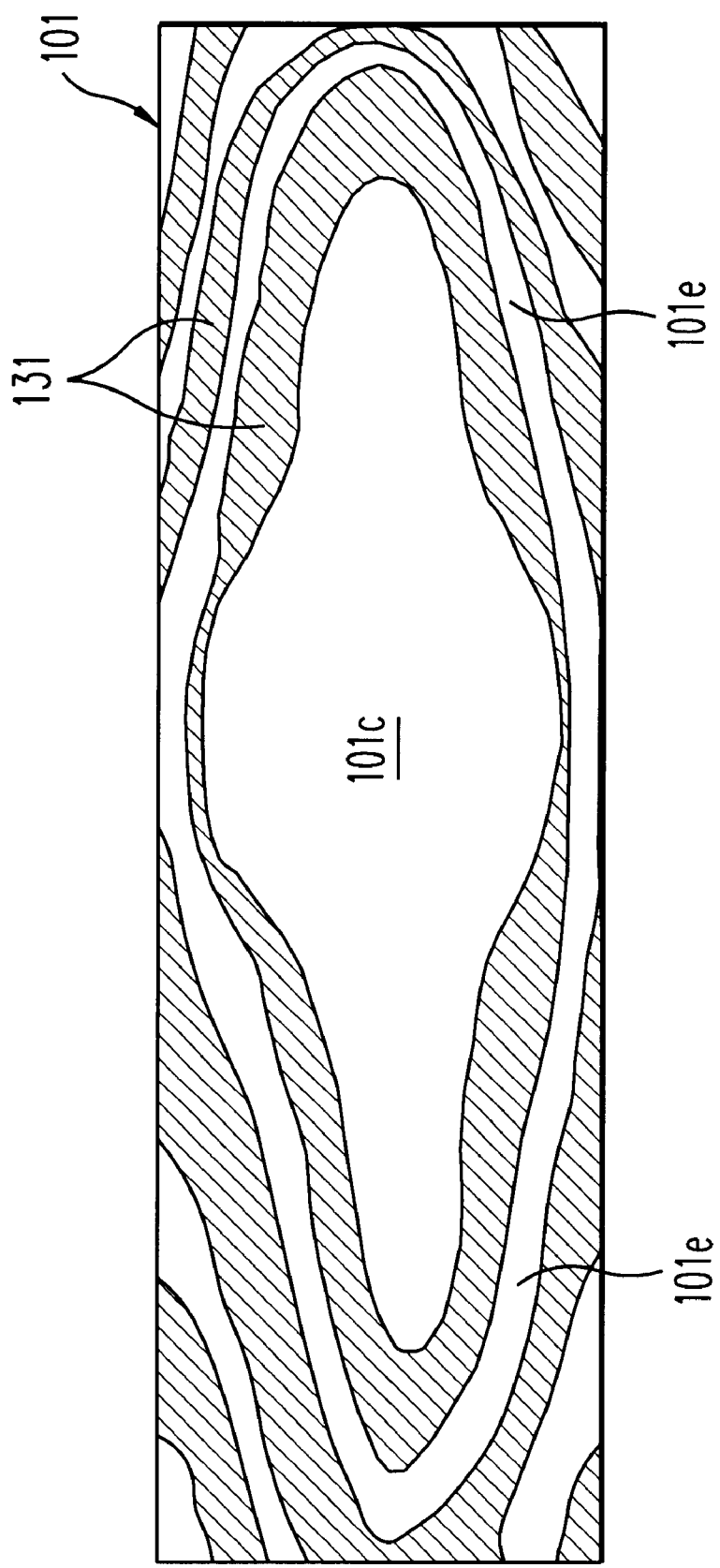
FIG. 9 is a front view showing optical elasticity interference stripes caused by birefringence of a detection lens.

Furthermore, regarding the optical elasticity interference fringes 131, for instance as shown in FIG. 9, the distance between the interference fringes 131 is wide on the center portion 101c of the lens while the distance therebetween is narrow on the circumferential edge portion 101e thereof. The distance between the interference fringes 131 is approximated to the pixel size of the CCD camera 112 or becomes narrower than the pixel size thereof on some occasions.

In such an area, even though the birefringence thereof in one pixel (an area corresponding to one pixel) of the CCD camera 112 has changed largely, since the average value thereof is inevitably output as the measurement value at that pixel, the reliability of the measurement value in that area is lowered.

Regarding this point, in the measurement apparatus of the present embodiment, the focal distance of the lens 116 is set to a long value in the area where the distance between the interference fringes 131 becomes narrow, and the focusing magnification rate of the focusing optical system 113 is raised, and thereby the interference fringes are enlarged. In such a state, the measurement is practiced. Consequently, the birefringence can be further precisely measured over the entire surface of the detection lens 101.

SIXTH EMBODIMENT

Figure 10:
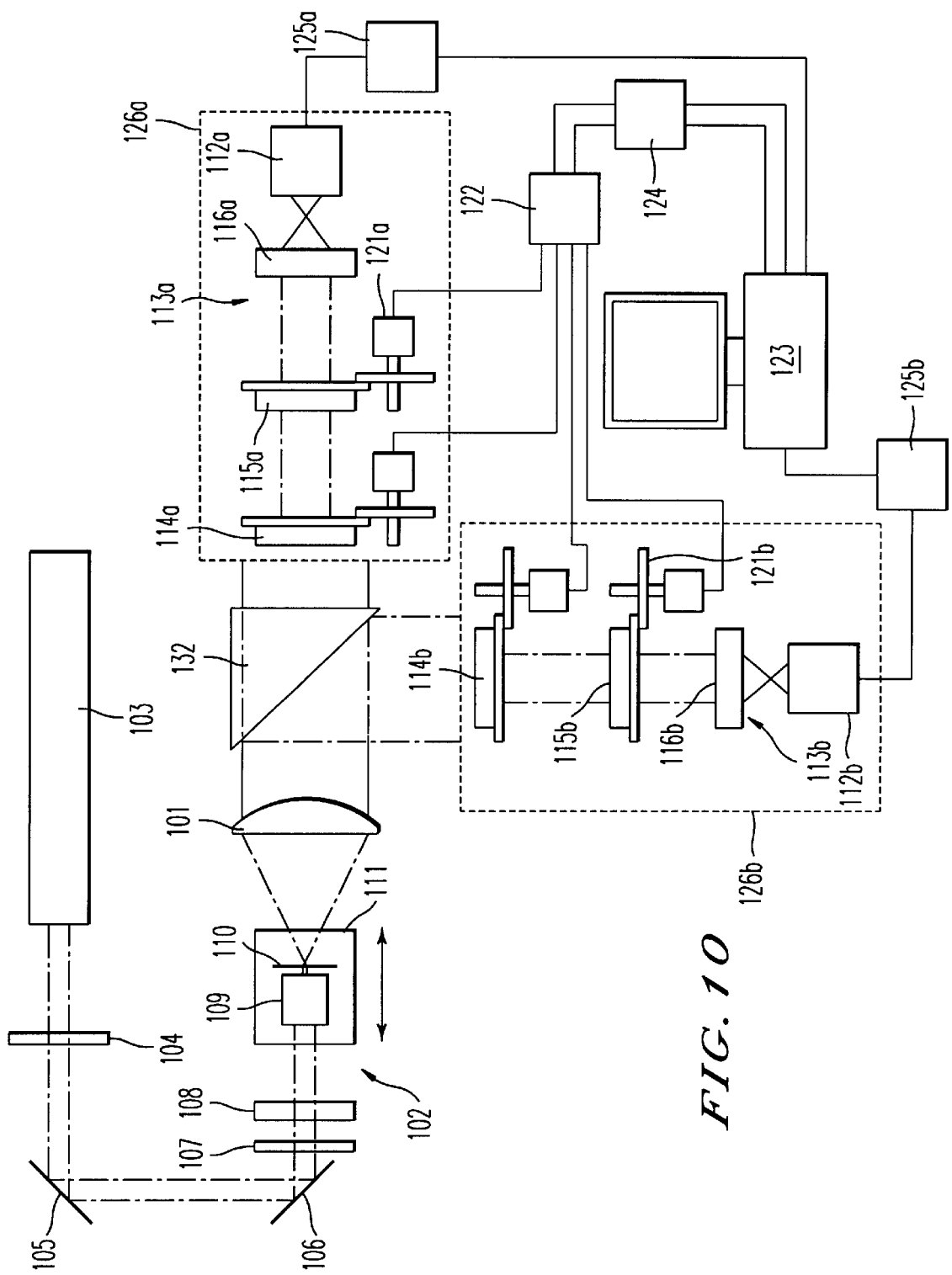
FIG. 10 is a structural view showing a sixth embodiment according to the present invention.

A sixth embodiment of the present invention is described hereinafter, referring to FIG. 10. Same reference numerals are attached to the same portions as in the fifth embodiment, and the descriptions thereof are omitted. The above is also true for the subsequent embodiment.

In the sixth embodiment, the light-receiving side displacement medium 130 constructed with the base 131, the guide 128, and the stepping motor 129, etc. as described in the fifth embodiment is omitted. Instead, two light-receiving units 126a and 126b of a same construction are newly provided as a light receiving unit Namely, the light-receiving unit 126a is constructed with a λ/4-plate 114a, polarization plate 115a, lens 116a, CCD camera 112a, and rotation medium 121a, while the other light-receiving unit 126b is constructed with a λ/4-plate 114b, polarization plate 115b, lens 116b, CCD camera 112b, and rotation medium 121b.

Furthermore, a prism 132 serving as a branching medium for branching transmission light from the detection lens 101 into two lights, and respectively directing the lights thus branched to the light-receiving units 126a and 126b as incident lights, is provided in the latter stage of the detection lens 101. Regarding the separation of the transmission light transmitted through the detection lens 101 by the action of the prism 132, the incident angle of the transmission light to the reflection surface of the prism is set to an angular value larger than the Brewster's angel of the prism 132, such that there occurs no difference of phase skipping between the p-polarizing light (the light vibrating in the direction parallel with the reflection surface of the prism 132) and the s-polarizing light (the light vibrating in the other direction perpendicular to the reflection surface of the prism 132). Moreover, fixed-focus lenses are used for the lenses 116a and 116b, and the positions of those lenses are respectively adjusted such that the vicinity of the detection lens 101 and the photographing surfaces of the CCD camera 112a and 112b are put substantially in a focusing relationship. A material in which almost all of the birefringence is removed, such as glass lens, can be used for the lenses 116a and 116b.

In such a structure, regarding the transmission light, transmitted through the detection lens 101 and branched by the prism 132, if each of the two light-receiving units 126a and 126b is disposed such that the transmission light from the different measured areas of the detection lens 101 is directed onto those light-received units 126a and 126b, the different measured areas of the detection lens 101 can be measured at the same time, and thereby the easiness of the operation can be improved.

As to the method of measurement, the images photographed by the two CCD cameras 112a and 112b are taken into the personal computer 123 through image inputting units 125a and 125b, and then the measurement is performed. The actual content of the processings thereof is the same as that described in the first embodiment. Consequently, according to the present embodiment, the entire surface of the detection lens 101 can be measured at the same time without moving the light-receiving units 126a and 126b.

Moreover, regarding the structure of a modification of the sixth embodiment, as in the case of the fifth embodiment, it may be allowable that a combination lens capable of changing the focal distance thereof constructed with a plurality of lenses is employed instead of the individual lenses 116a and 116b, and in such a structure, by changing the distance between the lenses constructing the combination lens, the focal distance of the combination lens is changed and each of the focusing magnification rates is also changed respectively and independently. Namely, if the positions of the lenses 116a and 116b are previously adjusted such that the focusing relationship is established with the vicinity of the detection lens 101, the focusing magnification rates of the focusing optical system 113a and 113b can be changed in the respective light-receiving units 126a and 126b in the state of keeping the focusing relationship.

Thereby, in the area where the distance between the interference fringes is narrowed in the measured area by the respective light-receiving units 126a and 126b, the focal distance of the lens 116a or the lens 116b is set to a long value. And then, the focusing magnification rates of the focusing optical systems 113a and 113b are increased. Thereby, the interference stripes are enlarged. And then, the lights are respectively focused on the CCD camera 112a and 112b and the measurement is performed in such a state. Consequently, a further accurate measurement can be performed in both of the light-receiving units 126a and 126b.

SEVENTH EMBODIMENT

The seventh embodiment of the present invention is described hereinafter, referring to FIGS. 11 through 13. In the seventh embodiment, regarding the lens 116 capable of changing the focal distance thereof (also same, regarding the lenses 116a and 116b capable of charging the focal distance, in the above-mentioned modification), the focal distance of the lens 116 (consequently, the focusing magnification rate of the focusing optical system 113) can be set automatically.

Figure 11:
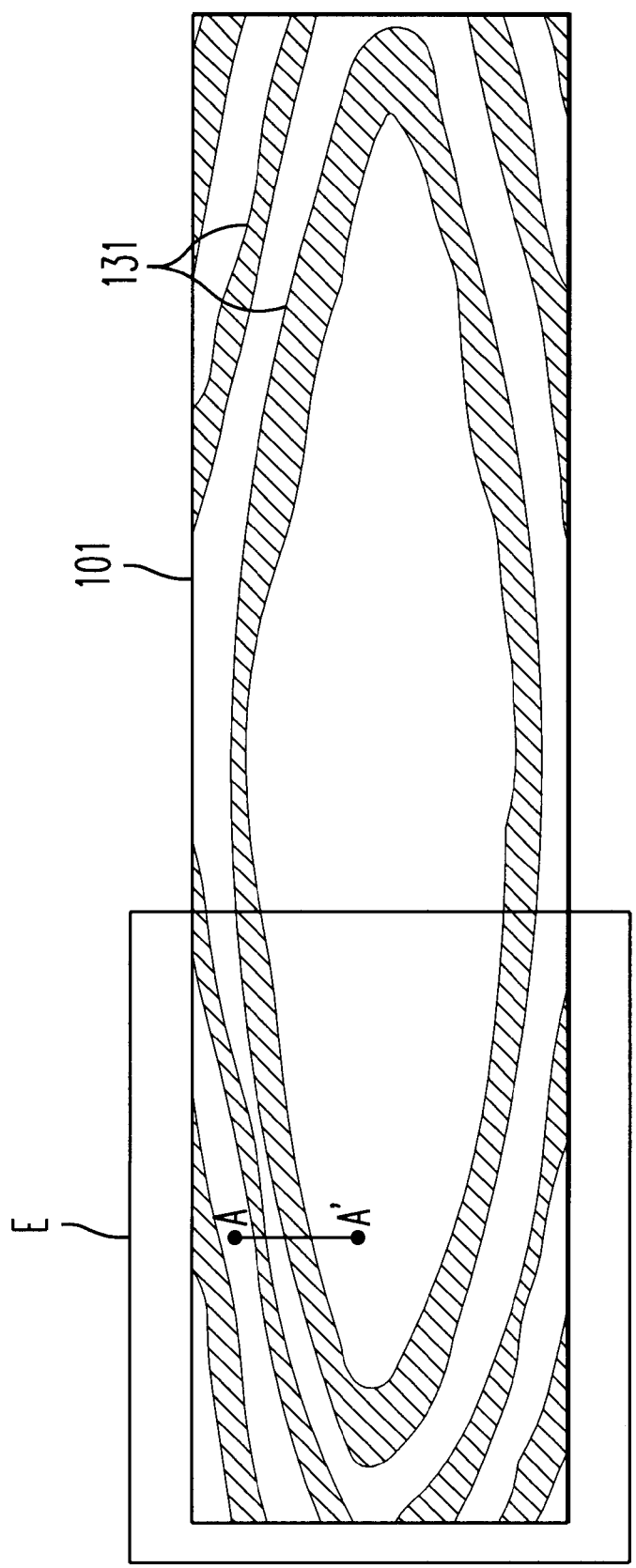
FIG. 11 is a front view showing a state of optical elasticity interference stripes photographed by a CCD camera in a seventh embodiment according to the present invention.

At first, the image of the optical elasticity interference fringes 131 of the detection lens 101 photographed by the CCD camera 112 is shown, for example, in FIG. 11. The symbol E represents the area of observing the image by use of the CCD camera 112.

Figure 12:
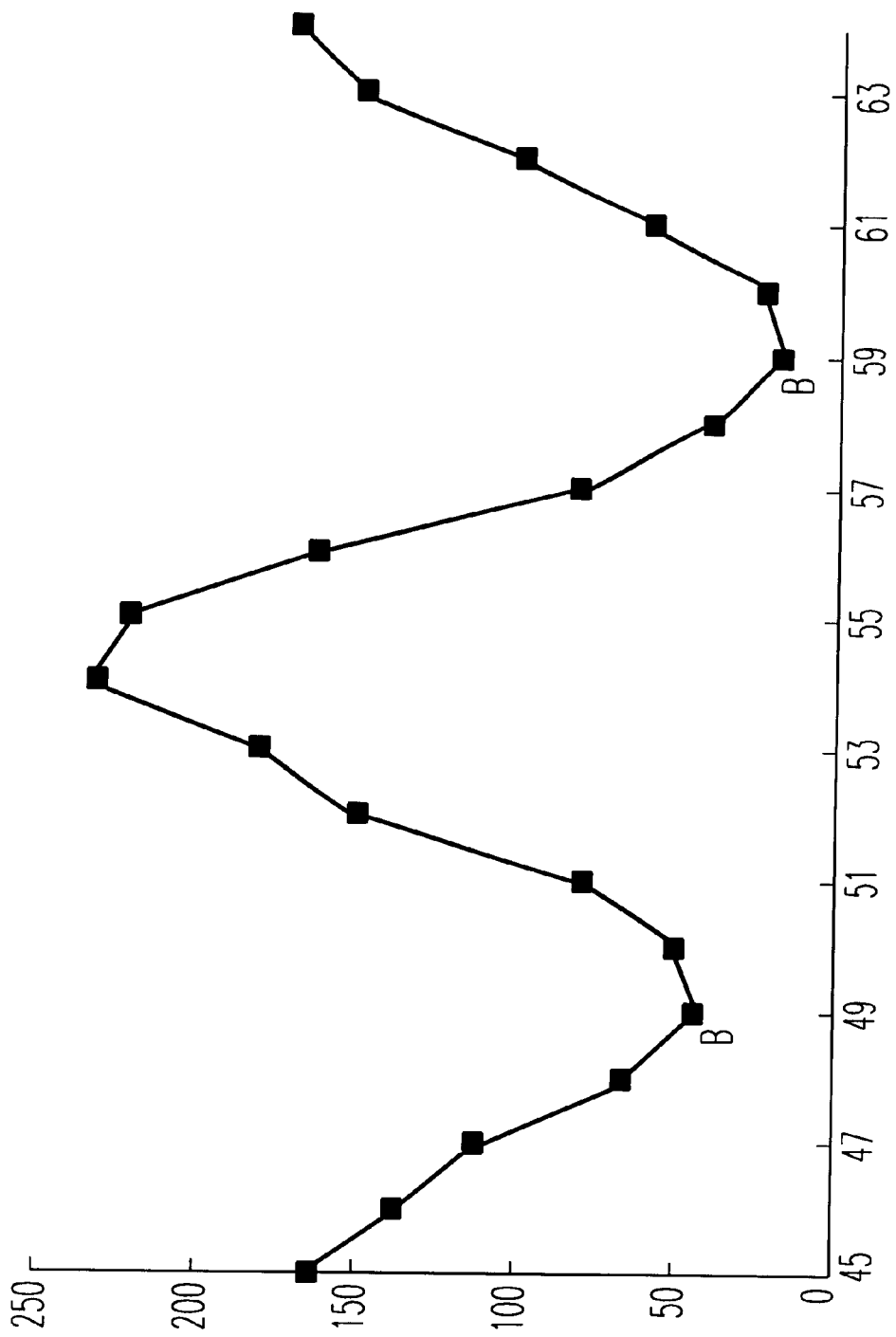
FIG. 12 is a graph illustrating the pixel density distribution on a cross-section taken along the line A–A' in FIG. 11.

FIG. 12 is a graph illustrating the pixel density distribution of the image on the cross-section taken along the A–A' line in FIG. 11. It is possible to presume that the distance between the minimum values (or the maximum value) of the pixel density distribution shown in FIG. 12 is the distance between the interference fringes. In the example as shown in FIG. 12, the above-mentioned distance corresponds to the distance between the points B and B'. The distance corresponds to ten pixels of the CCD camera 112.

In consideration of such photographing results thus obtained, if the distance between the minimum values (or the maximum values) of the pixel density distribution is not larger than, for instance, five pixels, the distance between the interference fringes becomes too narrow. As a result, the measured value turns out to be unreliable. In such a situation, regarding the distance between the minimum values (or the maximum values), a threshold value (for instance, five pixels) is previously set by the pixels number of the CCD camera 112. In the area to be measured where the distance between the minimum values (or the maximum values) is smaller than the above-mentioned threshold value, the distance between the lenses of the lens 116 capable of changing the focal distance is adjusted to make the focal distance thereof long such that the distance therebetween becomes larger than the threshold value. In such a way, the focusing magnification rate of the focusing optical system 113 is preferably raised.

Figure 13:
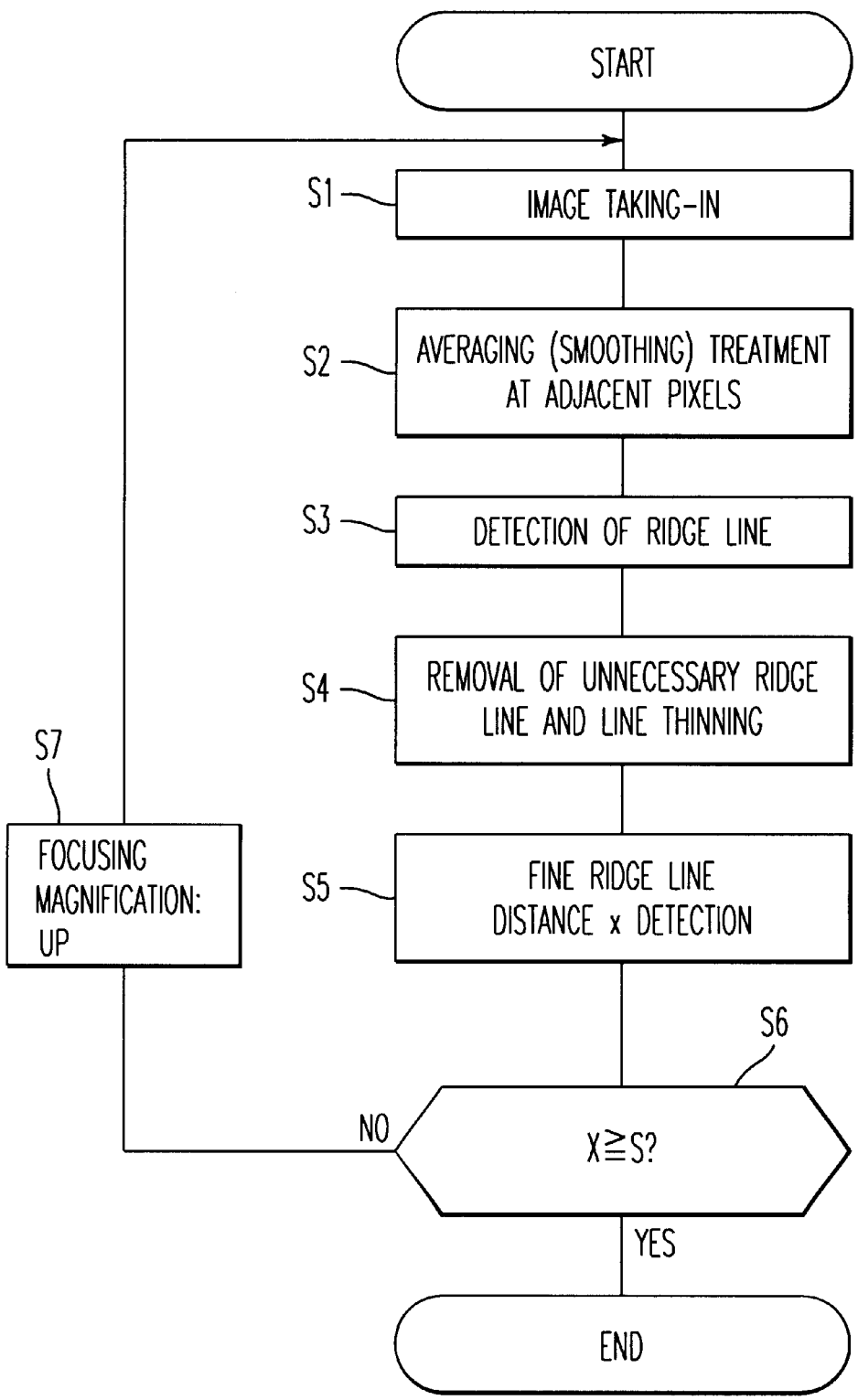
FIG. 13 is a flowchart illustrating a process of automatically setting a focusing magnification rate.

FIG. 13 is a flowchart illustrating the process of automatically setting the focusing magnification rate on the basis of such principles as mentioned heretofore. The word "ridge line" in the flowchart of FIG. 13 signifies the curve connecting, with each other, the positions taking the minimum value (or the maximum value) of the pixel density. The symbol "X" in the same flowchart signifies the distance between the positions on the ridge line respectively taking minimum values in the area E observed by the CCD camera 112. The above distance also corresponds to the distance between the interference fringes taking the minimum value in the area E observed by the CCD camera 112. The symbol "S" signifies the previously set threshold value of the fringes distance as the unit of the pixels number of the CCD camera 112.

At first, the image photographed by the CCD camera 112 is taken (step S1). Next, an averaging process (smoothing process) in the adjacent pixel is performed as a process of obtaining the minimum fringes distance in the area E observed by the CCD camera 112 (step S2). The ridge lines are then detected (step S3). The unnecessary ridge lines among all of the detected ridge lines are removed, and line-thinning is performed (step S4). Thereby, the minimum ridge lines distance X is detected (step S5). The detected minimum ridge lines distance X is compared with the threshold value S (step S6). When the detected minimum ridge lines distance X is smaller than the threshold value S, the process of increasing the focusing magnification rate is repeated (step S7). Finally, when the minimum ridge lines distance X becomes larger than the threshold value S, the measurement of the birefringence as mentioned before is started. Consequently, according to the present embodiment, the easiness of operation the measurement apparatus is improved, and in addition, it is possible to intend to make the focusing magnification rate in a suitable state.

Moreover, regarding the lens 116 composed of the lens combination capable of changing its focal distance, the adjustment of the distance between the individual construction lenses is preferably performed so as to change the focal distance as the lens combination in the state of keeping the focusing relationship between the vicinity of the detection lens 101 and the photographing surface of the CCD camera 117, for instance, by mounting the respective construction lenses on the stage and moving the stage by use of a driving source such as a motor. Otherwise, it is possible to utilize a zooming mechanism including a zooming lens generally available on the market.

According to a feature of the invention, the birefringence can be precisely measured over the entire surface of the detection lens. At the same time, it is easy to cope with a change of a type of the detection lens. Furthermore, a birefringence measuring apparatus of wide usefulness can be provided. In addition, a focusing magnification rate of the focusing optical system is set most suitably to match states of the birefringence occurrence which is different in accordance with the detection lens or the place of the detection lens. Consequently, the measurement can be performed precisely regardless of the state of the birefringence occurrence.

According to a further feature of the invention, if a plurality of light-receiving units are included, the entire detection lens can be measured at the same time without moving the light-receiving unit. In particular, according to such a feature of the invention, since the respective light-receiving units in the birefringence measuring apparatus are disposed as a branching medium to respectively receive transmission lights from different measured areas of the detection lens, the entire detection lens can be effectively measured at the same time and with easiness of operation.

According to a further feature of the invention, since the focusing magnification rates of the respective focusing optical systems can be independently changed per each of the respective light-receiving units, the focusing magnification rates are respectively set most suitably per each of the respective light-receiving units, so as to match states of the birefringence occurrence which are different in accordance with the detection lens or the place of the detection lens in the measured area. Thereby, the measurement can be performed further precisely regardless of the state of the birefringence occurrence.

According to a further feature of the invention, since a suitable focusing magnification rate can be automatically set on the basis of the data of the distance between the interference fringes in the transmission image from the practical detection lens, the easiness of operating the measurement apparatus is improved. In addition, it is possible to intend to make suitable the focusing magnification rate and resolution at low cost.

EIGHTH EMBODIMENT

Figure 14:
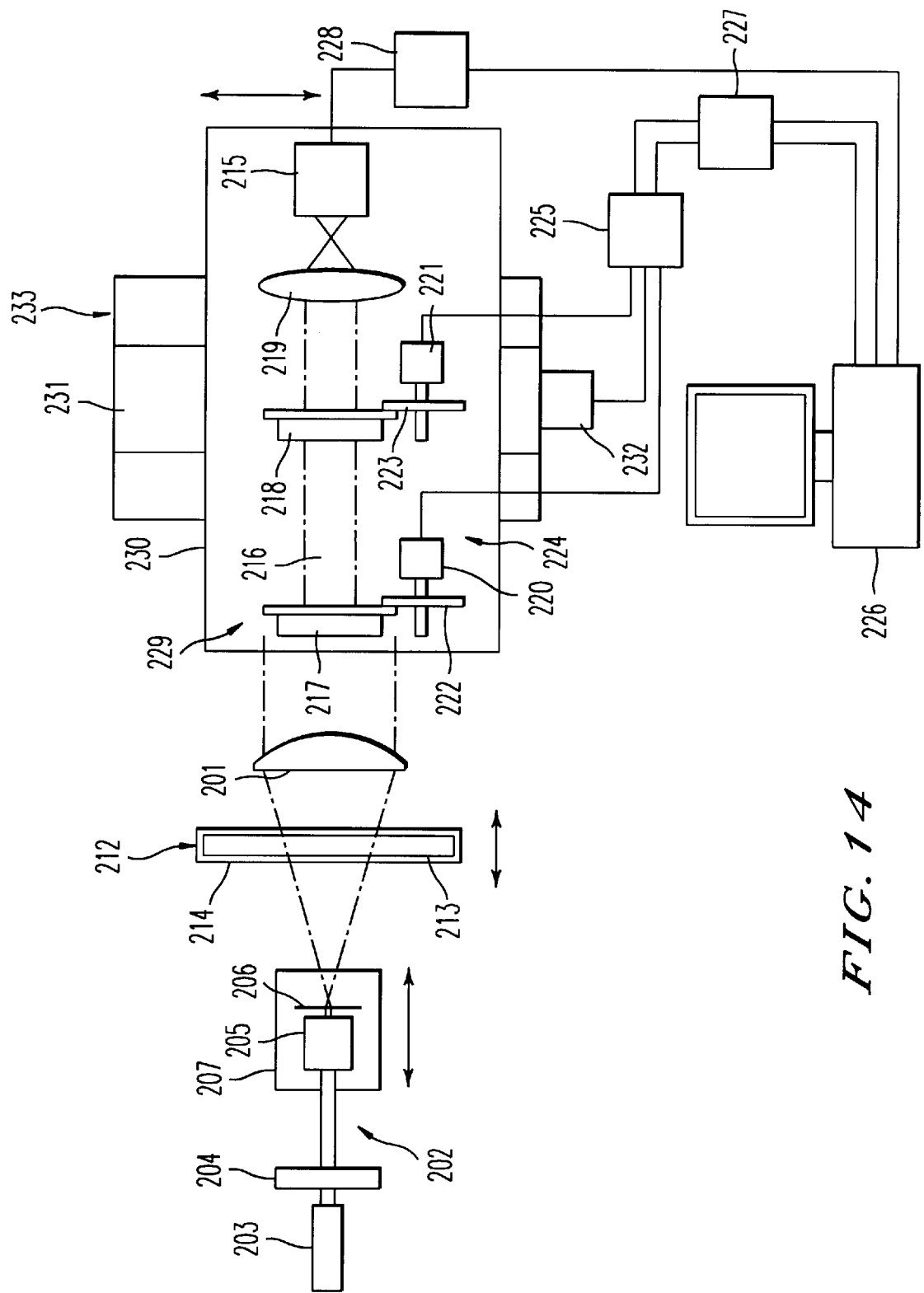
FIG. 14 is a structural view showing a eighth embodiment according to the present invention.

An eighth embodiment of the present invention is described hereinafter, referring to FIGS. 4, 14, 15A, and 15B. In FIG. 14 the detection lens 201 as the object to be measured in the eighth embodiment is an axis-asymmetrical lens respectively having different focal distances in the main scanning direction (direction parallel with the paper surface) and in the subscanning direction (direction perpendicular to the paper surface), and the detection lens 201 is held by a holder (not shown). At first, a radiation optical system 202 for radiating light onto the detection lens 201 in a state of predetermined polarization is provided for such a detection lens 201.

The above-mentioned radiation optical system 202 is constructed with a semiconductor laser 203 for emitting a straight-line polarization light beam having a short coherent length, a $\lambda/4$-plate 204 for converting the straight-line polarization light beam from the semiconductor laser 203 to a circular polarization light beam, a lens 205, and a pin hole 206.

The lens 205 equally serves as an object lens of a microscope and radiates diffusion light toward the detection lens 201. The pin hole 206 functions as a spatial filter. The lens 205 and the pin hole 206 are carried on the stage 207 which is capable of moving in the optical axis direction. The stage 207 carrying the lens 205 and tie pin hole 206 is moved back and forth in the optical axis direction by the rotation of a stepping motor (not shown) for driving the stage 207. In such a structure, a radiation-side displacement medium is constructed with the stage 207 and the stepping motor, etc., and the position of the lens 205 from the detection lens 201 in the direction of the optical axis thereof can be adjusted freely. Furthermore, a rotation origin position sensor is provided on the stepping motor. The distance between the lens 205 and the detection lens 201 is previously set to a predetermined distance. If the state is assumed to be a movement origin of the stage 207, the variation of the distance between the lens 205 and the detection lens 201 due to the movement of the stage 207 can be detected. In practice, the distance can be detected by a distance detecting medium on the basis of an operation of a number of pulses supplied to the stepping motor.

Furthermore, a compensation lens 213 constructing a compensation optical system 212 is provided on a position of the optical axis thereof between the radiation optical system 202 and the detection lens 201. The compensation lens 213 has an inverse property to that of the detection lens 201 in the main scanning direction and the subscanning direction. Namely, the compensation lens 213 has a refraction force only in the subscanning direction, that is, the direction perpendicular to the surface of the paper. Namely, the compensation lens has a function of converting the transmission light transmitted through the detection lens 201 to a parallel light flux (collimating the light).

The compensation lens 213 is also carried on a stage 214 capable of moving in the optical axis direction thereof. The stage 214 is moved back and forth in the same direction by the rotation of a stepping motor (not shown) for driving the stage 214. Here, a compensation system displacement medium is constructed with the stage 214, and the stepping motor, etc., and the position of the compensation lens 213 from the detection lens 201 in the optical axis direction thereof. Furthermore, a rotation origin position sensor is mounted on the stepping motor. The distance between the compensation lens 213 and the detection lens 201 is previously set to the predetermined distance. Assuming that the state is the movement origin, the change of the distance between the compensation lens 213 and the detection lens 201 caused by the movement of the stage 214 can be detected by counting the number of the pulses supplied to the stepping motor. In practice, the distance can be detected by the distance detecting medium on the basis of an operation of counting the number of pulses supplied to the stepping motor by the personal computer 226 as discussed below.

Furthermore, a CCD camera 215 serving as an array-state light-receiving element for receiving transmission light is provided on the optical axis at the transmission/emission side of the detection lens 201. A focusing optical system 216 is provided between the detection lens 201 and the CDD camera 215.

The focusing optical system 216 is constructed with a λ/4 plate 217 for converting the light flux of the elliptic polarization approximated to straight-line polarization by action of the birefringence at the time of passing through the detection lens 201, and a focusing lens 219 for focusing the light passing through the polarization plate 218 serving as the polarization element. The position of the lens 219 is previously adjusted such that a focusing relationship is established between the vicinity of the detection lens 201 surface and the CCD camera 215. As to the material of the lens 219, a material such as glass is employed because in a glass lens the birefringence inside thereof can be sufficiently removed.

Furthermore, for the λ/4-plate 217 and the polarization plate 218, stepping motors 220 and 221 and the gear systems thereof 222 and 223 for respectively rotating the λ/4-plate 217 and the polarization plate 218 around the light advancing direction are provided for a rotation medium 224. Sensors (not shown) for sensing the position of the rotation origin are respectively mounted on the stepping motors 220 and 221. The sensors respectively count the number of the pulses of the stepping motors 220 and 221. Thereby, the respective rotation angles of the λ/4-plate 217 and the polarization plate 218 can be detected. In practice, the respective rotation angles of the λ/4-plate 217 and the polarization plate 218 can be detected by the rotation angle detecting medium on the basis of an operation of counting the number of the pulses supplied to the stepping motors in the personal computer 226 as discussed below. The reference numeral 225 represents a motor driver for driving the stepping motors 220 and 221. The motor driver 225 receives pulses from the personal computer 226 and the pulse generator 227 and drives the stepping motors respectively.

Furthermore, the image data photographed by the CCD camera 215 are taken into the memory of the personal computer 226 through an image inputting unit 228. And then, the birefringence phase difference of the detection lens 201 and the azimuth of the main axis is calculated by a predetermined method of the operational calculation on the basis of the rotation angle data of the image data and the positions of the stepping motors 220 and 221.

In such a way, the function of the operational calculation medium for calculating the birefringence of the detection lens 201 is practiced by the operational calculation processing function performed by the computer unit represented by the CPU included in the personal computer 226. In this connection, the image photographed by the CCD camera 215 is displayed on the monitor of the personal computer 226 or on another specially-used monitor.

Furthermore, the λ/4-plate 217, the polarization plate 218, the lens 219, the CCD camera 215, and the rotation medium 224 are carried on a common base 230 as a light-receiving unit 229. The common base 230 can be moved by a guide 231 in the direction substantially perpendicular to the optical axis of the measurement optical system (namely, in FIG. 14, the up-and-down direction as shown by the arrow mark). The common base 230 is driven to be displaced by the stepping motor 232. Here, a light-receiving side displacement medium 233 for moving and adjusting the light-receiving unit 223 in the direction perpendicular to the optical axis thereof is constructed with the common base 230, the guide 231, the stepping motor 232, etc.

In such a structure, at first, it is assumed that, in the measurement optical system as shown in FIG. 14, the vicinity of the surface of the detection lens 201 and the photographing surface of the CCD camera 215 are put substantially in a focusing relationship by the lens 219. For this reason, the spatial image of the optical elasticity interference stripes occurring in the vicinity on the surface of the detection lens 20 is photographed by the CCD camera 215 through the polarization plate 218 by the action of the birefringence of the detection lens 201. However, since diffusion light radiated onto the detection lens 201 is made substantially parallel (collimated) by the detection lens 201, the size (square measure) of the spatial image of the optical elasticity interference fringes occurring in the vicinity of the detection lens 201 turns out to be almost equal to that of the detection lens 201.

On the other hand, the size (square measure) of the λ/4-plate 217 and the polarization plate 218 both constructing the measurement optical system is almost 50 mm in diameter at a maximum. It is impossible to transmit once the spatial image of the optical elasticity fringes having a size exceeding the above-mentioned size of the λ/4-plate 217 and the polarization plate 218. As a result, when the diameter of the detection lens 201 becomes large, the measurement of the birefringence over the entire surface of the detection lens 201 turns out to be impossible. Regarding this point, it may be allowable that the size of the spatial image of the optical elasticity interference fringes is reduced once, and thereafter the spatial image is transmitted through the polarization plate 218.

However, on this occasion, since the measurement optical system becomes complicated, and in addition the size of the spatial image of the optical elasticity interference fringes is reduced, the spatial resolution at the time of the measurement is lowered. Furthermore, in a case that the birefringence of the detection lens 201 is large, the distance between the optical elasticity interference fringes becomes narrower than the size of the CCD camera 215. And therefore, the measurement itself turns out to be impossible on some occasions.

For this reason, in the present embodiment, all of the optical system elements composed of the λ/4-plate 217 and other elements subsequent thereto are unitarily combined into one unit as a light-receiving unit 229, and the unitarily combined unit is moved in a direction substantially perpendicular to the optical axis of the optical system. The spatial image of the optical elasticity interference stripes having almost the same size as that of the detection lens 201 is partially divided into some pieces, and those pieces of the image thus divided are observed by the CCD camera 215. In such a way, the measurement is performed.

For instance, as shown in FIG. 4, at first, the base 230 is moved by the stepping motor 232 so as to enable observing the measurement area E1 of the detection lens 201. In such a state, the phase difference and the main axis compass direction are measured as mentioned below. Following this step, the base 230 is further moved by the stepping motor 232 to enable observing the measurement area E2 of the detection lens 201. In such a state, the phase difference and the main axis azimuth are measured in the same way. And then, the base 230 is further moved by the stepping motor 232 to enable observing the measurement area E3 of the detection lens. In such a state, the phase difference and the main axis azimuth are measured in the same way.

Moreover, when the measurement area of the detection lens 201 is determined, for instance, moving the base 230, the optical elasticity interference fringes photographed and monitored by the CCD camera 215 are observed and one suitable area among the areas E1–E3 is preferably selected. Or otherwise, the apparatus is structured such that a rotation origin position sensor is mounted on the stepping motor 232, and thereby the movement distance of the base 230 can be detected by the number of the pulses supplied to the stepping motor 232. In such a structure, the measurement area can be determined previously and the base 230 is automatically moved to the position on which the measurement area can be observed. In the latter case, the movement distance of the base 230, that is, the polarization plate 218, etc. can be detected by the distance detecting medium, in practice, on the basis of an operation of counting the number of the pulses supplied to the stepping motor 232 in the personal computer 226.

In such a way, it is possible to measure the birefringence of the entire detection lens 201 without lowering the resolution, according to the basic structure and operation of the present embodiment.

Here, the state of setting the birefringence measuring apparatus in the case of the present embodiment is described hereinafter. At first, the compass direction of the polarization of the semiconductor laser 203 is set to the direction horizontal on (parallel with) the paper surface, and the compass direction of the λ/4-plate 204 is set to the direction inclined by 45° from the paper surface. In such a setting, a circular-polarization light can be radiated onto the detection lens 201.

Before starting the measurement, for instance, the azimuth of the λ/4-plate 217 is set to the direction inclined by 45° from the horizontal direction parallel with the paper surface. In the state of not setting the detection lens 201, rotating the compass direction of the polarization place 218, the setting of the azimuth angle of the polarization plate 218 is performed to minimize the intensity of the transmission light from the polarization plate 218 (namely, to make darkest the transmission light). In other words, the setting is performed such that the azimuth of the polarization of the semiconductor laser 203 becomes almost perpendicular to that of the polarization plate 218. The angle of the azimuth is stored in the memory as the rotation angle at the time of measurement.

On this occasion, if the parallel (collimated) light flux is not directed onto the λ/4-plate 217, the rotation origin position of the polarization plate 218 is not precisely obtained. Therefore, it is necessary to make parallel (collimate) the light flux directed onto the λ/4-plate 217 as the incident light. However, usually, it may be allowable that the glass lens of a same shape as that of the detection lens 201 having apparently no birefringence is temporarily set on the position of the detection lens 201, and the light rays directed to the polarization plate 218 and the CCD camera 215 as the incident light are made parallel (collimated). Or otherwise, it may also be allowable that the detection lens 201 and the lens 205 are taken removed from the measuring apparatus, and in such a state the light rays directed to the polarization plate 218 and the CCD camera 215 are made parallel (collimated).

In the practical measurement, at first, the detection lens 201 is held with a holder and set on a predetermined position. The polarization plate 218 is rotated from the position of the rotation origin by every $(180/n)°$ in the state that the azimuth of the λ/4-plate 237 is on the inclination of 45° from the direction parallel with the paper (document) surface. The symbol "in" represents the number of the previously set measurement points.

Here, every time the polarization plate 218 is rotated by $(180/n)°$, the CCD image data read out by the CCD camera 215 is taken into the memory of the personal computer 226. Thereby, the rotation angle date of the polarization plate 218 and n sheets of the CCD image data can be acquired.

Next, the azimuth of the λ/4-plate 217 is set to 0° with respect to the paper (document) surface, and as in the aforementioned case of rotating the polarization plate 217 by every $(180/n)°$ from the position of the rotation origin, the CCD image data are taken into the memory of the personal computer 226, and thereby the rotation angle data of the polarization plate 218 and n sheets of the CCD image data can be acquired. In such a way, the birefringence of the detection lens 201 can be obtained by performing the operational calculation process according to the following procedure by use of the operational calculation medium, on the basis of 2n sheets of the CCD image data and the rotation angle data of the polarization plate 218.

Now, the situation of the polarization state variation of the optical system in the measurement apparatus shown in FIG. 14 is represented by use of the Mueller matrix. Assuming that the Mueller matrix of the circular polarization light directed to the detection lens 201 as the incident light is L, the Mueller matrix of the detection lens 201 is T, the Mueller matrix of the λ/4-plate 217 is Q, and the Mueller matrix of the polarization plate 218 is A, Stokes' parameter S can be obtained from the above factors and others.

At first, the Stokes' parameter S45 at the time of setting the azimuth of the λ/4-plate 217 is set to the angle of 45° against the horizontal direction on the ground surface.

$$S_{45} = A \cdot Q_{45} \cdot T \cdot L = \frac{1}{2}\begin{pmatrix} 1 & \cos2\theta & \sin2\theta & 0 \\ \cos2\theta & \cos^2 2\theta & \sin2\theta\cos2\theta & 0 \\ \sin2\theta & \sin2\theta\cos2\theta & \sin^2 2\theta & 0 \\ 0 & 0 & 0 & 0 \end{pmatrix}\begin{pmatrix} 1 & 0 & 0 & 0 \\ 0 & 0 & 0 & -1 \\ 0 & 0 & 1 & 0 \\ 0 & 1 & 0 & 0 \end{pmatrix}\downarrow \quad (21)$$

$$\rightarrow \begin{pmatrix} 1 & 0 & 0 & 0 \\ 0 & 1-(1-\cos\delta)\sin^2\phi & (1-\cos\delta)\sin2\phi\cos2\phi & -\sin\delta\sin2\phi \\ 0 & (1-\cos\delta)\sin2\phi\cos2\phi & 1-(1-\cos\delta)\cos^2\theta & \sin\delta\cos2\phi \\ 0 & \sin\delta\sin2\phi & -\sin\delta\cos2\phi & \cos\delta \end{pmatrix}\begin{pmatrix} 1 \\ 0 \\ 0 \\ -1 \end{pmatrix} =$$

$$\frac{1}{2}\begin{pmatrix} 1 + \cos\delta\cos2\theta - \sin\delta\cos2\phi\sin2\theta \\ \cos2\theta + \cos\delta\cos^2 2\theta - \sin\delta\cos2\phi\sin2\theta\cos2\theta \\ \sin2\theta + \cos\delta\sin2\theta\cos2\theta - \sin\delta\cos2\phi\sin^2\theta \\ 0 \end{pmatrix}$$

From the equation (21), the light intensity I45 obtained on the CCD camera 215 can be calculated in accordance with the equation (22).

$$I_{45} = \frac{1}{2}(1 + \cos\delta\cos2\theta - \sin\delta\cos2\phi\sin2\theta) \quad (22)$$

In the equations (21) and (22), $\theta$ is the main axis compass direction of the polarization plate 218, $\delta$ is the birefringence phase difference of the detection lens 201, and $\phi$ is the main axis compass direction of the detection lens 201.

When the polarization plate 218 is rotated by the stepping rotor 221, the value of $\theta$ in those equations changes, and the light intensity I45 in the equation (22) obtained by the CCD camera 215 also changes. The phase $\phi45$ of the light intensity variation due to the rotation of the polarization plate 218 in the main axis compass direction can be obtained by the equation (23) as shown below from practically measured CCD image data and the rotation angle data of the polarization plate 218.

$$\phi_{45} = \tan^{-1}\left\{\frac{2R\sum(I_{45i} \cdot \sin\theta_i)}{2R\sum(I_{45i} \cdot \cos\theta_i)}\right\} \quad (23)$$

Next, the phase $\phi0$ of the light intensity variation at the time of setting the azimuth of the $\lambda/4$-plate 217 0° from the direction parallel with the paper surface paper surface in the way as described below. The Stoke's parameter S0 is represented by the equation (24) in the similar manner.

$$SO = A \cdot Q_0 \cdot T \cdot L = \frac{1}{2}\begin{pmatrix} 1 & \cos2\theta & \sin2\theta & 0 \\ \cos2\theta & \cos^2 2\theta & \sin2\theta\cos2\theta & 0 \\ \sin2\theta & \sin2\theta\cos2\theta & \sin^2 2\theta & 0 \\ 0 & 0 & 0 & 0 \end{pmatrix}\begin{pmatrix} 1 & 0 & 0 & 0 \\ 0 & 1 & 0 & 0 \\ 0 & 0 & 0 & 1 \\ 0 & 0 & -1 & 0 \end{pmatrix}\downarrow \quad (24)$$

$$\rightarrow \begin{pmatrix} 1 & 0 & 0 & 0 \\ 0 & 1-(1-\cos\delta)\sin^2\phi & (1-\cos\delta)\sin2\phi\cos2\phi & -\sin\delta\sin2\phi \\ 0 & (1-\cos\delta)\sin2\phi\cos2\phi & 1-(1-\cos\delta)\cos^2 2\phi & \sin\delta\cos2\phi \\ 0 & \sin\delta\sin2\phi & -\sin\delta\cos2\theta & \cos\delta \end{pmatrix}\begin{pmatrix} 1 \\ 0 \\ 0 \\ -1 \end{pmatrix} =$$

$$\frac{1}{2}\begin{pmatrix} 1 + \sin\delta\sin2\phi\cos2\theta - \cos\delta\sin2\theta \\ \cos2\theta + \sin\delta\sin^2 2\theta - \cos\delta\sin2\theta\cos2\theta \\ \sin2\theta + \sin\delta\sin2\phi\sin2\theta\cos2\theta - \cos\delta\sin^2\theta \\ 0 \end{pmatrix}$$

From the equation (24), the light intensity I0 obtained on the CCD camera 215 is represented by the equation (25).

$$I_0 = \frac{1}{2}(1 + \sin\delta\sin2\phi\cos2\theta - \cos\delta\sin2\theta) \quad (25)$$

In the equations (24) and (25), $\theta$ is the main axis compass direction of the polarization plate 218, $\delta$ is the birefringence phase difference of the detection lens 201, and $\phi$ is the main axis azimuth of the detection lens 201.

The phase $\phi0$ of the variation of the light intensity I0 in accordance with the rotation of the main axis azimuth of the polarization plate 218 can be obtained by the equation (26), as in the case of the equation (23).

$$\phi_0 = \tan^{-1}\left\{\frac{2R\sum (I_{0i} \cdot \sin\theta_i)}{2R\sum (I_{0i} \cdot \cos\theta_i)}\right\} \quad (26)$$

Changing the equations (22) and (25), the phases φ45 and φ0 are obtained by the following equations (27) and (28).

$$\phi_{45} = \tan^{-1}(\tan\delta\cos 2\phi) \quad (27)$$

$$\phi_0 = \tan^{-1}\left(\frac{1}{\tan\delta\sin 2\theta}\right) \quad (28)$$

Consequently, from the equations (23), (26), (27), and (28), the phrase difference δ and the main axis azimuth φ can be obtained by the following equations (29) and (30).

$$\delta = \tan^{-1}\sqrt{\tan^2\phi_{45} + \frac{1}{\tan^2\phi_0}} \quad (29)$$

$$\phi = \frac{1}{2}\tan^{-1}\left(\frac{1}{\tan\phi_0\tan\phi_{45}}\right) \quad (30)$$

Consequently, according to the present embodiment, in the manner basically according to the rotative analyzer method, the transmission light transmitted through the detection lens 201 is directed to the polarization plate 218 for changing the polarization state as the incident light. Rotating the polarization plate 218, the light is received and detected by the CCD camera 215, and thereby the birefringence of the detection lens 201 is calculated. In such a situation, the distance between the lens 205 of the radiation optical system 202 for radiating the diffusion light onto the detection lens 201 and the detection lens 201 can be optionally set. Observing the transmission image transmitted through the detection lens 201 the distance between the detection lens 201 and the lens 205 is adjusted. Thereby, it is possible to obtain optical elasticity interference fringes of the transmission image of the detection lens 201 which at most are slightly effected by the optical distortion. Furthermore, the measurement of the birefringence can be precisely performed over the entire surface of the detection lens 201. At the same time, it is possible to easily cope with a change of a type of the detection lens 201. In such a way, a widely-usable apparatus for and method of measuring the birefringence can be realized.

Furthermore, regarding the light source of such a measuring apparatus, since the polarization plate 218, etc. has a waveform dependability, it may be more preferable to use a monocolor laser light source than to use a white-color light source including the lights of source various wavelength. However, if light having a long coherent length such as an He—Ne laser is used as the laser light source, interference fringes of noise due to the multiple reflection, etc. occur in the measurement optical system in addition to the optical elasticity interference stripes occurring due to the birefringence of the detection lens 201, and since the former interference fringes are superposed on the latter interference fringes (optical elasticity interference fringes), that may result in a measurement error occurrence on some occasions. Regarding this point, in the present embodiment, if a semiconductor laser 203 having a short coherent length is used as the light source, it may be possible to obtain an effect of preventing the occurrence of interference fringes of noise due to the multiple reflection, etc. in the measurement optical system.

Here, the operation of the compensation lens 213 in the compensation optical system 212 for making parallel (collimating) the transmission light transmitted through the detection lens 201 which is added in the present embodiment is described hereinafter, referring to FIGS. 15A and 15B.

Basically, in a case that the detection lens 201 is an axis-symmetrical lens, even though the compensation lens 213 is not provided therein, the focal point of the lens 205 is made to substantially coincide with that of the detection lens 201. Thereby, since the lens 205 and the detection lens 201 construct the a focal system, the transmission light transmitted through the detection lens 201 turns out to be substantially parallel (substantially collimated).

However, in a case that the detection lens 201 as employed in the present embodiment is an axis-asymmetrical lens having different focal distances in the main scanning direction and in the subscanning direction, since the focal point of the lens 205 cannot be made, at the same time, to respectively coincide with the focal points of the detection lens 201 in both of the main scanning directions, it is difficult inevitably to radiate the axis-symmetrical spherical surface wave onto the detection lens 201 and thereby make parallel (collimate) the transmission light of the detection lens 201.

Regarding this point, in the present embodiment, a compensation lens 213 having a refraction force only in the subscanning direction is disposed between the lens 205 and the detection lens 201. In such a structure, the diffusion light created by the lens 205 is converted to the axis-asymmetrical light, and thereafter, the light thus converted is radiated onto the detection lens 201.

Figure 15A:
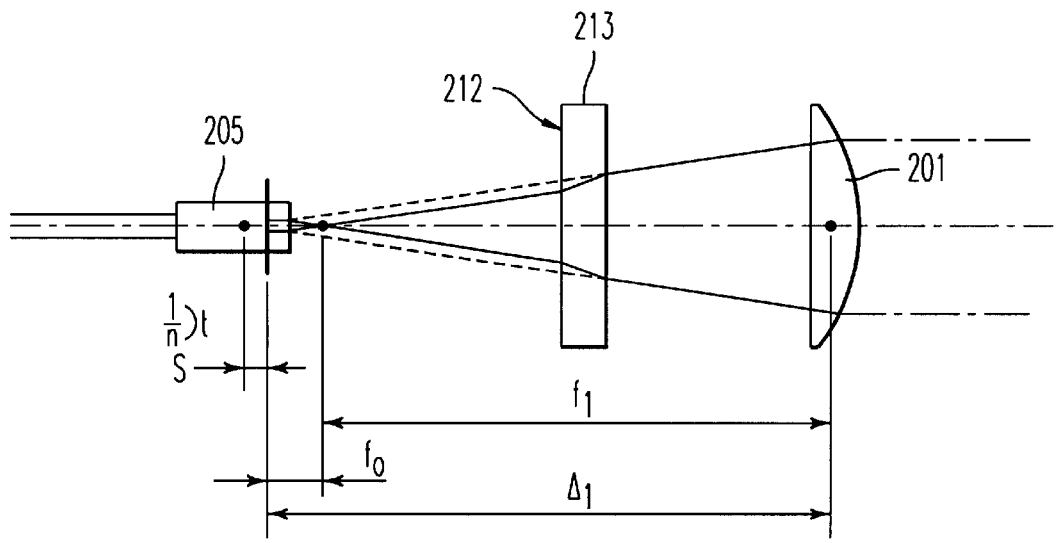
FIG. 15A is a plan view in the main scanning direction and FIG. 15B is a side view looked at in the subscanning direction.
Figure 15B:
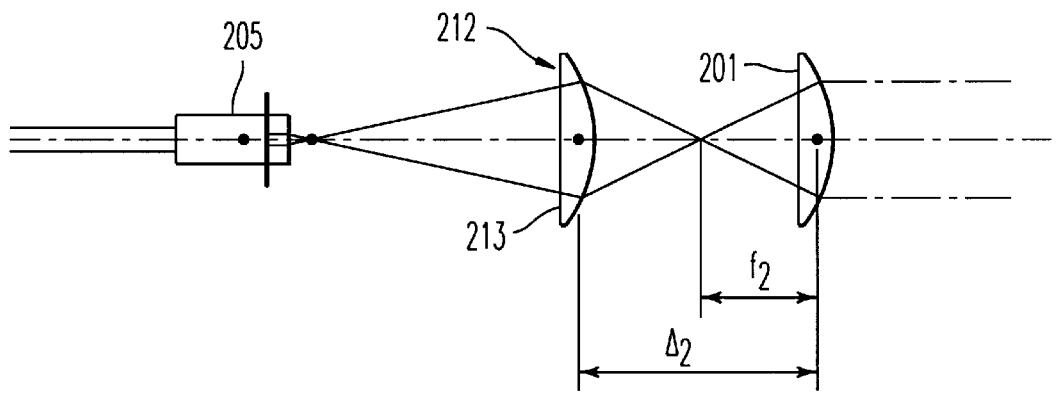

Here, as shown in FIG. 15 (FIGS. 15A and 15B), it is assumed that the focal distance of the detection lens 201 in the main scanning direction is f1, the focal distance thereof in the subscanning direction is f2 (f1>f2), the focal distance of the lens 205 is f0, the focal distance of the compensation lens 213 in the subscanning direction is f8 (the focal distance thereof in the main scanning direction is infinite), the thickness thereof is t, the refraction index thereof is n8, the distance between the lens 205 and the detection lens 201 (distance between the main points thereof) is Δ1, and the distance between the compensation lens 213 and the detection lens 201 is Δ2. Under the above assumptions, if the distances Δ1 and Δ2 are set so as to satisfy the following equations (31) and (32), the transmission light transmitted through the detection lens 201 is made substantially parallel (substantially collimated).

$$\Delta_1 = f_0 + f_1\left(1 - \frac{1}{n_8}\right) \quad (31)$$

$$f_1 - t\left(1 - \frac{1}{n_8}\right) = \frac{f_8(\Delta_2 - f_2)}{\Delta_2 - f_2 - f_8} + \Delta_2 \quad (32)$$

Here, regarding such setting of the distances, for instance, the states in which the lens 205 and the detection lens 201, and the compensation lens 213 and the detection lens 201, respectively make an approach closest to each other are respectively assumed to be the movement origins thereof, by respectively moving the stages 211 and 214 from the respective movement origins, the distance Δ1 between the lens 205 and the detection lens 201 and the distance Δ2 between the compensation tens 213 and the detection lens 201 can be respectively detected.

In fact, in the case of limiting the sort of the detection lens 201, since it is not necessary to move the compensation lens 213 in the optical axis direction thereof, it may be allowable to previously set the optical system such that the distances Δ1 and Δ2 satisfy the equations (31) and (32) without providing the stage 214.

NINTH EMBODIMENT

The ninth embodiment of the present invention is described hereinafter, referring to FIG. 16. Same reference numerals are attached to the same parts as that shown in the eighth embodiment, and the explanations thereof are omitted. The same is true for the subsequent embodiment.

The detection lens 241 to be measured in the present embodiment is assumed to be a lens of very long focal distance. On this occasion, in order to construct a focal system with the lens 205 and the detection lens 241, it is necessary to set the distance therebetween to a very large value. For this reason, there arises a problem to be solved that the apparatus inevitably turns out to be large-sized.

However, if such a detection lens 241 is regarded as a flat plate having both surfaces almost parallel with each other and the parallel (collimated) light is radiated thereon, it can be avoided that the measurement apparatus becomes large-sized. In the present ninth embodiment, the structure thereof is shown in FIG. 16 as an example.

Figure 16:
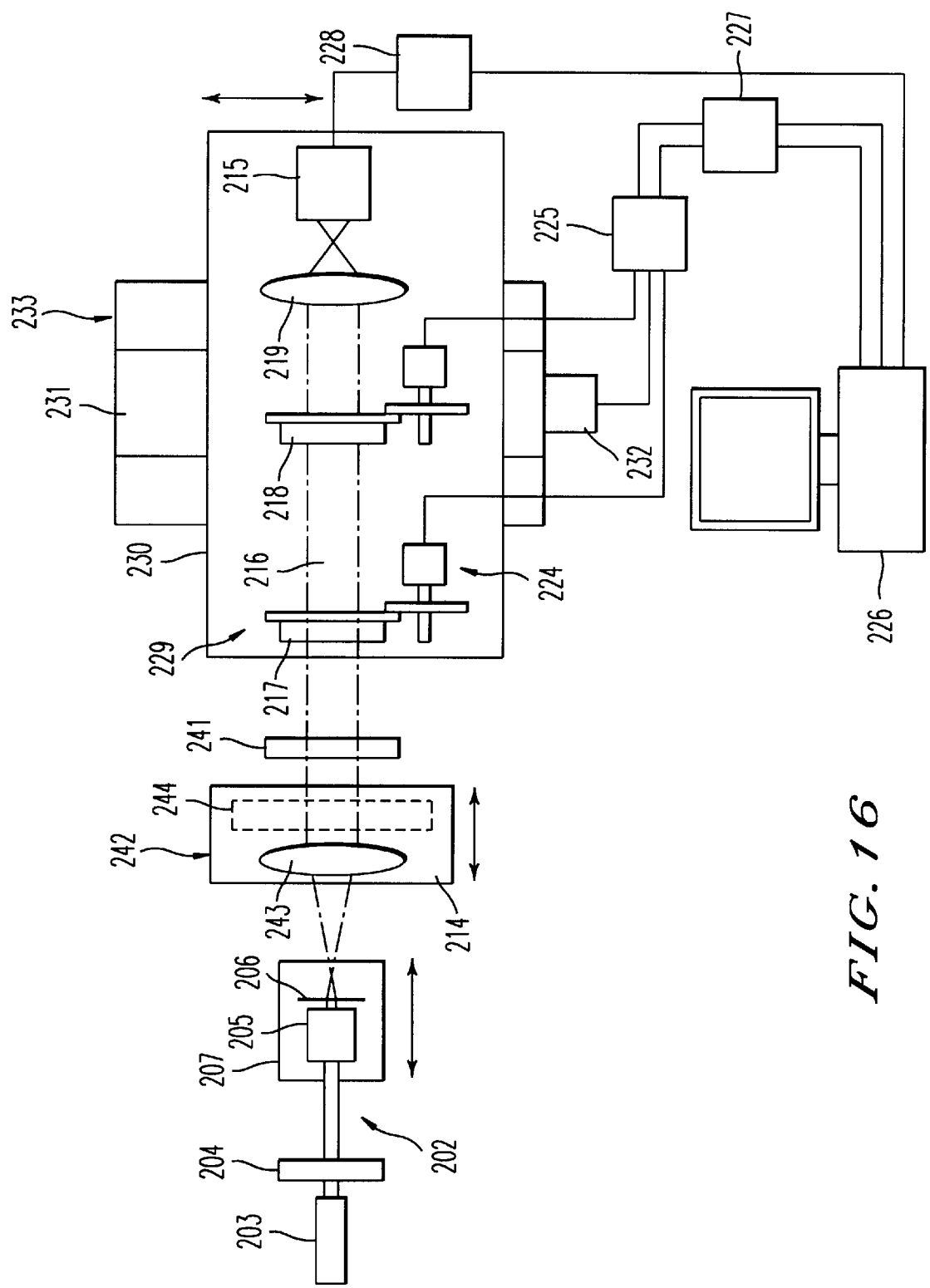
FIG. 16 is a structural view showing a ninth embodiment according to the present invention.

Namely, in FIG. 16, a compensation lens 243 constructing a compensation optical system 242 is provided on the optical axis thereof between the lens 205 in the radiation optical system 202 and the detection lens 241. The compensation lens 243 is an ordinary axis-symmetrical convex lens having a function of converting light radiated on the detection lens 241 and the light transmitted therethrough to parallel light flux. Such a compensation lens 243 is also carried on a stage 214, and the stage 214 can be moved and adjusted in the direction of the optical axis thereof.

In such a structure, the diffusion light created by the lens 205 is converted to parallel light flux by the compensation lens 243, and thereafter the light flux thus converted is radiated onto the detection lens 241. At this time, since the detection lens 241 is not a parallel flat plate in practice, the light transmitted through the detection lens 241 is shifted from the route of the parallel light flux. Such transmission light becomes diffusion light or convergence light. However, if the focal distance of the detection lens 241 is sufficiently long, since the displacement angle of the transmission light transmitted through the detection lens 241 is sufficiently long, since the displacement angle of the transmission light transmitted through the detection lens 241 from the path of the parallel-light flux becomes very small, the measurement error due to the above displacement can be neglected. Consequently, even though the detection lens 241 to be measured has a very long focal distance, the measurement can be performed without making the apparatus large-sized, and wide usefulness of the device thereof can be raised.

Here, in the present embodiment, for instance, in a case that the detection lens 241 has different focal distances in the main scanning direction and the subscanning direction, and the lens 241 can be regarded as a parallel flat plate in the main scanning direction and the lens 241 cannot be regarded as the parallel flat plate in the subscanning direction, it may be allowable that the compensation optical system 242 is constructed with the combination of a compensation lens 243 and another compensation lens 244. The compensation lens 244 has an optical property different from that of the compensation lens 243. Here, an axis-asymmetrical lens having a refraction force only in the subscanning direction is employed as the compensation lens 244. In such a structure, it is possible to radiate the light onto the detection lens 241 so as to convert the light flux transmitted through the detection lens 241 to a parallel light flux.

Therefore, to view as a general consideration, if the compensation optical system is constructed with a combination of plural optical elements respectively having different optical properties, such a structure can cope with the detection lens having a very long focal distance, and in addition, it is possible to make substantially parallel the transmission light even for an axis-asymmetrical detection lens. Thereby, wide usefulness of the apparatus is realized.

Furthermore, for instance, in the structure as shown in FIG. 16, the compensation lenses 243 and 244 can be respectively taken away, or the lenses 243 and 244 can be replaced by the lenses of other types (lenses of different focal distance and/or diameter). By adopting such a structure, the possibility of coping with a change of a type of the used detection lens 241 can be further widened and the wide usefulness of the apparatus can be further realized.

TENTH EMBODIMENT

Figure 17:
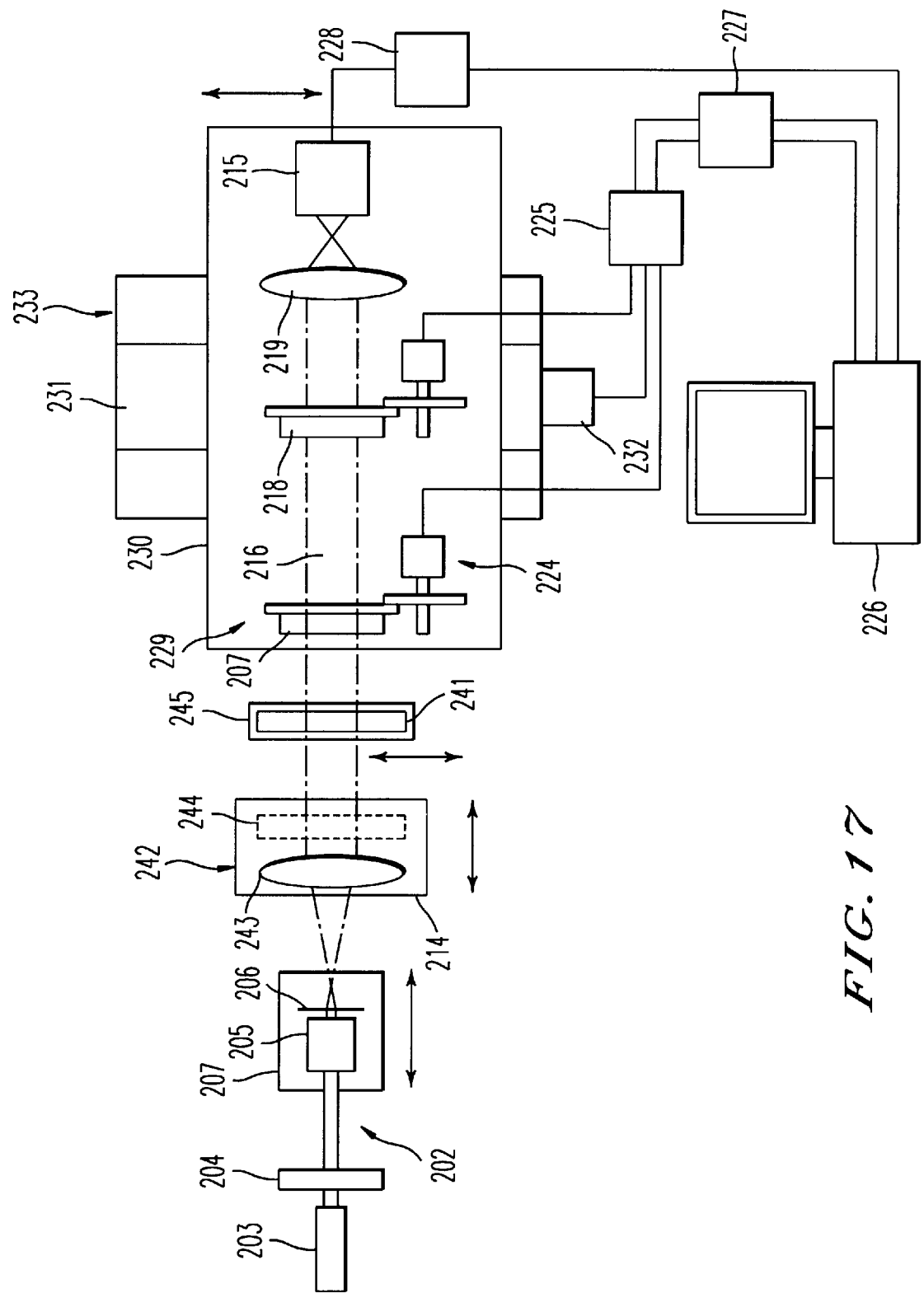
FIG. 17 is a structural view showing a tenth embodiment according to the present invention.

The tenth embodiment of the present invention is described hereinafter, referring to FIG. 17. The tenth embodiment can also be applied to the eighth embodiment as shown in FIG. 14. Here, the tenth embodiment is applied to a birefringence measuring apparatus and the method of measuring the birefringence as shown in FIG. 16 employing the detection lens 241.

In the tenth embodiment, the detection lens 241 is carried on a stage 245 capable of moving in the direction perpendicular to the optical axis thereof. The stage 245 is moved in the direction perpendicular thereto by the rotation of the stepping motor (not shown) for driving the stage 245. Here, the lens displacement medium is constructed with the stage 245 and the stepping motor, etc. The adjustment of the position in the direction perpendicular to the optical axis of the detection lens 241 so as to match the measurement area on the detection lens 241.

In such a structure, by moving the detection lens 241 by use of the stage 245 in the direction perpendicular to the optical axis thereof, the incident position of the parallel light flux from the compensation optical system side 242 to the detection lens 241 is gradually changed, and at the same time, the area of the entire detection lens 241 is divided and measured.

Namely, the method of dividing and measuring the area according to the tenth embodiment is the same as the method of dividing and measuring the area by moving the light-receiving unit side 223 as explained with respect to FIG. 14 in the direction perpendicular to the optical axis so as to match the measured area. Only the situation is reversed such that the light-receiving unit side 229 is fixed and the detection lens side 241 is made movable.

According to a feature of the invention, the birefringence can be measured precisely over the entire surface of the detection lens. At the same time, it is possible to cope with a change of the type of the detection lens. Furthermore, even in a case that the focal distances of the detection lens differ from each other in the main scanning direction and in the subscanning direction, the compensation optical system including a lens having different focal distances in the main scanning direction and in the subscanning direction is added to a latter stage of the radiation optical system. In such a structure, the light flux transmitted through the detection lens can be made almost parallel. Thereby, the aforementioned measurement of the birefringence can be made possible without damaging a normal operation of the optical elements subsequent to the polarization element, and wide usefulness of the measurement apparatus can be realized.

According to a further feature of the invention, regardless of a case in which the focal distances of the detection lens differ from each other in the main scanning direction and in the subscanning direction, even in a case that the focal distance of the lens is long, the compensation optical system is constructed with plural optical elements having different optical properties, for instance, such as the abomination of the axis-asymmetrical lens and the ordinary axis-symmetrical lens. In such a structure, it is possible to freely cope with a change of the type of the detection lens and the wide usefulness can be further realized.

According to features of the invention, even in a case that the focal distance of the detection lens is long, the detection lens is moved in the direction perpendicular to the optical axis thereof, and thereby the area of the entire detection lens can be divided and measured. Consequently, the measurement of the birefringence of the entire detection lens can be realized at low cost without lowering the resolution.

Obviously, numerous other embodiments or numerous modifications of the present invention are possible in light of the above teachings. It is therefore to be understood that, within the scope of the appended claims, the present invention may be practiced otherwise than as specifically described herein. Having thus fully described the invention, it will be apparent to one of ordinary skill in the art that many changes and modifications can be made thereto without departing from the spirit and scope of the invention as set forth herein.

This document is based on Japanese Patent applications Nos. JPAP 10-111, 813/1998, JPAP 10-111, 814/1998, and JPAP 10-207, 764/1998, respectively filed on Apr. 22, Apr. 22, and Jul. 23, 1998, the entire contents of which are herein incorporated by reference.

What is claimed is:

1. A birefringence measuring apparatus comprising:
    a radiation optical system configured to radiate diffusion light onto a detection lens in a predetermined polarization state;
    a displacement medium configured to move and adjust a position of said radiation optical system in a direction of an optical axis with respect to said detection lens;
    a polarization element configured to change the polarization state of transmission light transmitted from said detection lens;
    a rotation angle detection medium configured to detect an angle of rotating said polarization element;
    an array-state light-receiving element configured to receive light transmitted through said polarization element;
    a focusing optical system configured to focus the light transmitted through said polarization element on said array-state light-receiving element; and
    an operational calculation medium configured to calculate birefringence of said detection lens based on the rotation angle detected by said rotation angle detecting medium and an output of the light focused on said array-state light-receiving element.

2. A birefringence measuring apparatus as defined in claim 1, further comprising:
    a light-receiving-side displacement medium configured to move and adjust a unitary combination of said polarization element, said focusing optical system, and said array-state light-receiving element in a direction substantially perpendicular to the optical axis.

3. A birefringence measuring apparatus as defined in claim 2, further comprising:
    a distance detecting medium configured to detect a movement distance of the unitary combination.

4. A birefringence measuring apparatus as defined in claim 1, further comprising:
    an angle changing medium configured to change an angle of the unitary combination of said polarization element, said focusing optical system, and said light-receiving element with respect to an advancing direction of the transmission light transmitted from said detection lens; and
    an angle detecting medium configured to detect the angle of the unitary combination.

5. A birefringence measuring apparatus as defined in claim 2, further comprising:
    an angle changing medium configured to change an angle of the unitary combination of said polarization element, said focusing optical system, and said light-receiving element with respect to an advancing direction of the transmission light transmitted from said detection lens; and
    an angle detecting medium configured to detect the angle of the unitary combination.

6. A birefringence measuring apparatus is defined in claim 3, further comprising:
    an angle changing medium configured to change an angle of the unitary combination of said polarization element, said focusing optical system, and said light-receiving element with respect to an advancing direction of the transmission light transmitted from said detection lens; and
    an angle detecting medium configured to detect the angle of the unitary combination.

7. A birefringence measuring apparatus as defined in claim 1, further comprising:
    a light intercepting member configured to intercept light transmitted through a circumferential edge portion of said detection lens; and
    a light intercepting member moving medium configured to move said light intercepting member.

8. A birefringence measuring apparatus as defined in claim 2, further comprising:
    a light intercepting member configured to intercept light transmitted through a circumferential edge portion of said detection lens; and
    a light intercepting member moving medium configured to move said light intercepting member.

9. A birefringence measuring apparatus as defined in claim 3, further comprising:
    a light intercepting member configured to intercept light transmitted through a circumferential edge portion of said detection lens; and
    a light intercepting member moving medium configured to move said light intercepting member.

10. A birefringence measuring apparatus as defined in claim 4, further comprising:
    a light intercepting member configured to intercept light transmitted through a circumferential edge portion of said detection lens; and
    a light intercepting member moving medium configured to move said light intercepting member.

11. A birefringence measuring apparatus as defined in claim 5, further comprising:
 a light intercepting member configured to intercept light transmitted through a circumferential edge portion of said detection lens; and
 a light intercepting member moving medium configured to move said light intercepting member.

12. A birefringence measuring apparatus as defined in claim 6, further comprising:
 a light intercepting member configured to intercept light transmitted through a circumferential edge portion of said detection lens; and
 a light intercepting member moving medium configured to move said light intercepting member.

13. A method of measuring birefringence of a detection lens, comprising the steps of:
 adjusting a distance in a direction of an optical axis of a radiation optical system with respect to the detection lens disposed at a predetermined position;
 radiating, at a same time as the step of adjusting, diffusion light in a predetermined polarization state by said radiation optical system onto said detection lens;
 rotating a polarization element for changing the polarization state of transmission light transmitted from said detection lens in an advancing direction of the transmission light;
 detecting a rotation angle of said polarization element at a same time as the step of rotating;
 focusing light transmitted through said polarization element on a light-receiving surface of an array-state light-receiving element by use of a focusing optical system; and
 calculating birefringence of said detection lens based on of the detected rotational angle of said polarization element and an output of the light which is focused on said array-state light-receiving element.

14. A method of measuring birefringence of a detecting lens as defined in claim 13,
 wherein a unitary combination of said polarization element, said focusing optical system, and said light-receiving element is moved and adjusted in a direction substantially perpendicular to an optical axis, and is further moved and adjusted to be fitted to an area to be measured on said detection lens.

15. A method of measuring birefringence of a detecting lens as defined in claim 13,
 wherein an angle of the unitary combination of said polarization element, said focusing optical system, and said light-receiving element is changed with respect to an advancing direction of light transmitted through an area to be measured on said detection lens.

16. A method of measuring birefringence of a detecting lens as defined in claim 14,
 wherein an angle of the unitary combination of said polarization element, said focusing optical system, and said light-receiving element is changed with respect to an advancing direction of light transmitted through an area to be measured on said detection lens.

17. A method of measuring birefringence of a detection lens as defined in claim 13, further comprising the steps of:
 intercepting light transmitted through a circumferential edge area of said detection lens with a light intercepting member; and
 adjusting and setting a position of said light intercepting member to eliminate stray light transmitted through said circumferential edge portion of said detection lens.

18. A method of measuring birefringence of a detection lens as defined in claim 14, further comprising the steps of:
 intercepting light transmitted through a circumferential edge area of said detection lens with a light intercepting member; and
 adjusting and setting a position of said light intercepting member to eliminate stray light transmitted through said circumferential edge portion of said detection lens.

19. A method of measuring birefringence of a detection lens as defined in claim 15, further comprises the steps of:
 intercepting light transmitted through a circumferential edge area of said detection lens with a light intercepting member; and
 adjusting and setting a position of said light intercepting member to eliminate stray light transmitted through said circumferential edge portion of said detection lens.

20. A method of measuring birefringence of a detection lens as defined in claim 16, further comprises the steps of:
 intercepting light transmitted through a circumferential edge area of said detection lens with a light intercepting member; and
 adjusting and setting a position of said light intercepting member to eliminate stray light transmitted through said circumferential edge portion of said detection lens.

21. A birefringence measuring apparatus comprising:
 a radiation optical system configured to radiate diffusion light onto a detection lens in a predetermined polarization state;
 a displacement medium configured to move and adjust a position of said radiation optical system in an optical axis direction with respect to said detection lens;
 a polarization element configured to change the polarization state of transmission light transmitted from said detection lens;
 a rotation medium configured to rotate said polarization element around an advancing direction of said transmission light;
 a rotation angle detection medium configured to detect an angle of rotating said polarization element by said rotation medium;
 an array-state light-receiving element configured to receive light transmitted through said polarization element;
 a focusing optical system configured to change a focusing magnification of the light transmitted through said polarization element and which is focused onto a light-receiving surface of said array-state light-receiving element;
 a light-receiving-side displacement medium configured to move and adjust a unitary combination of said polarization element, said rotation medium, said array-state light-receiving element, and said focusing optical system in a direction substantially perpendicular to the optical axis; and
 an operational calculation medium configured to calculate birefringence of said detection lens based on the rotation angle detected by said rotation angle detecting medium and an output of the light which is focused on said array-state light-receiving element.

22. A birefringence measuring apparatus comprising:
 a radiation optical system configured to radiate diffusion light onto a detection lens in a predetermined polarization state;
 a displacement medium configured to adjust a position of said radiation optical system in a direction of an optical axis with respect to said detection lens;

a plurality of light-receiving units constructed, as one unit, with a polarization element configured to change the polarization state of transmission light transmitted from said detection lens;

a rotation medium configured to rotate said polarization element around an advancing direction of said transmission light;

a rotation angle detecting medium configured to detect an angle of rotating said polarization element by said rotation medium;

an array-state light-receiving element configured to receive light transmitted through said polarization element;

a focusing optical system configured to change a focusing magnification of light transmitted through said polarization element and which is focused on a light-receiving surface of said array-state light-receiving element;

a branching medium configured to branch the transmission light from said detection lens and directing said branched transmission light as incident light to respective of said light-receiving units; and an operational calculation medium configured to calculate birefringence of said detection lens based on the rotation angle detected by said rotation angle detecting medium in said respective light-receiving units and an output of the light which is focused on said array-state light-receiving element.

23. A birefringence measuring apparatus as defined in claim 22,
wherein said respective light-receiving units are arranged through said branching medium to respectively receive light transmitted from different areas to be measured of said detection lens.

24. A birefringence measuring apparatus as defined in claim 22,
wherein in said focusing optical system, the focusing magnification is independently changed per each of said respective light-receiving units.

25. A birefringence measuring apparatus as defined in claim 23,
wherein, in said focusing optical system, the focusing magnification is independently changed per each of said respective light-receiving units.

26. A birefringence measuring apparatus as defined in claim 21,
wherein, in said focusing optical system, the focusing magnification is automatically set based on a transmission image from said detection lens obtained at a time of focusing the transmission light from said detection lens on the light-receiving surface of said array-state light-receiving element.

27. A birefringence measuring apparatus as defined in claim 24,
wherein, in said focusing optical system, the focusing magnification is automatically set based on a transmission image from said detection lens obtained at a time of focusing the transmission light from said detection lens on the light-receiving surface of said array-state light-receiving element.

28. A birefringence measuring apparatus as defined in claim 25,
wherein, in said focusing optical system, the focusing magnification is automatically set based on a transmission image from said detection lens obtained at a time of focusing the transmission light from said detection lens on the light-receiving surface of said array-state light-receiving element.

29. A birefringence measuring apparatus comprising:
a radiation optical system configured to radiate diffusion light onto a detection lens in a predetermined polarization state;

a displacement medium configured to move and adjust a position of said radiation optical system in a direction of an optical axis with respect to said detection lens;

a compensation optical system disposed at a radiation side of said detection lens and configured to convert transmission light transmitted from the detection lens to substantially parallel light;

a polarization element configured to change the polarization state of the transmission light transmitted from said detection lens;

a rotation medium configured to rotate said polarization around an advancing direction of said transmission light;

a rotation angle detection medium configured to detect an angle of rotating said polarization element by said rotation medium;

an array-state light-receiving element configured to receive light transmitted through said polarization element;

a focusing optical system configured to change a focusing magnification of the light transmitted through said polarization element and which is focused on a light-receiving surface of said array-state light-receiving element; and an operational calculation medium configured to calculate birefringence of said detection lens based on the rotation angle detected by said rotation angle detecting medium and an output of the light which is focused on said array-state light-receiving element.

30. A birefringence measuring apparatus as defined in claim 29,
wherein said compensation optical system includes a combination of plural optical elements respectively having different optical properties.

31. A birefringence measuring apparatus as defined in claim 29, further comprising:
a lens displacement medium configured to move and adjust said detection lens in a direction perpendicular to the optical axis.

32. A birefringence measuring apparatus as defined in claim 30, further comprising:
a lens displacement medium configured to move and adjust said detection lens in a direction perpendicular to the optical axis.

33. A method of measuring birefringence of a detection lens, comprising the steps of:
disposing the detection lens at a predetermined position to move and adjust in a direction perpendicular to an optical axis;

adjusting a distance between said detection lens and a radiation optical system in the optical axis;

adjusting a position of a direction perpendicular to the optical axis of said detection lens to fit an area to be measured on said detection lens;

radiating light of a predetermined polarization state on said detection lens through a compensation optical system by said radiation optical system for the area to be measured of said detection lens;

causing substantially parallel transmission light to emit from said detection lens;

rotating a polarization element for changing the polarization state of the transmission light emitted from said detection lens around an advancing direction of the transmission light;

detecting, at a same time as the step of rotating, a rotation angle of said polarization element;

focusing light transmitted through said polarization element on a light-receiving surface of an array-state light-receiving element by use of a focusing optical system; and calculating birefringence of the area to be measured of said detection lens based on the detected rotation angle of said polarization element and an output of the light which is focused on said array-state light-receiving element.

34. A birefringence measuring apparatus comprising:

radiation optical system means for radiating diffusion light onto a detection lens in a predetermined polarization state;

displacement means for moving and adjusting a position of said radiation optical system means in a direction of an optical axis with respect to said detection lens;

polarization element means for changing the polarization state of transmission light transmitted from said detection lens;

rotation means for rotating said polarization element means around an advancing direction of said transmission light;

rotation angle detection means for detecting an angle of rotating said polarization element by said rotation means;

array-state light-receiving element means for receiving light transmitted through said polarization element means;

focusing optical system means for focusing the light transmitted through said polarization element means on said array-state light-receiving element means;

operational calculation means for calculating birefringence of said detection lens based on the rotation angel detected by said rotation angle detecting means and an output of the light which is focused on said array-state light-receiving element means.

35. A birefringence measuring apparatus as defined in claim 34, further comprising:

light-receiving-side displacement means for moving and adjusting a unitary combination of said polarization element means, said focusing optical system means, and said light-receiving element means in a direction substantially perpendicular to the optical axis.

36. A birefringence measuring apparatus as defined in claim 35, further comprising:

distance detecting means for detecting a movement distance by said light-receiving-side displacement means.

37. A birefringence measuring apparatus as defined in claim 34, further comprising:

angle changing means for changing an angle of a unitary combination of said polarization element means, said focusing optical system means, and said light-receiving element means with respect to the advancing direction of the transmission light transmitted from said detection lens; and angle detecting means for detecting the angle of the unitary combination.

38. A birefringence measuring apparatus as defined in claim 35, further comprising:

angle changing means for changing an angle of the unitary combination of said polarization element means, said focusing optical system means, and said light-receiving element means with respect to the advancing direction of the transmission light transmitted from said detection lens; and angle detecting means for detecting the angle of the unitary combination.

39. A birefringence measuring apparatus as defined in claim 36, further comprising:

angle changing means for changing an angle of the unitary combination of said polarization element means, said focusing optical system means, and said light-receiving element means with respect to the advancing direction of the transmission light transmitted from said detection lens; and angle detecting means for detecting the angle of the unitary combination.

40. A birefringence measuring apparatus as defined in claim 34, further comprising:

light intercepting means for intercepting light transmitted through a circumferential edge portion of said detection lens; and light intercepting means moving means for moving said light intercepting means.

41. A birefringence measuring apparatus as defined in claim 35, further comprising:

light intercepting means for intercepting light transmitted through a circumferential edge portion of said detection lens; and light intercepting means moving means for moving said light intercepting means.

42. A birefringence measuring apparatus as defined in claim 36, further comprising:

light intercepting means for intercepting light transmitted through a circumferential edge portion of said detection lens; and light intercepting means moving means for moving said light intercepting means.

43. A birefringence measuring apparatus as defined in claim 37, further comprising:

light intercepting means for intercepting light transmitted through a circumferential edge portion of said detection lens; and light intercepting means moving means for moving said light intercepting means.

44. A birefringence measuring apparatus as defined in claim 38, further comprising:

light intercepting means for intercepting light transmitted through a circumferential edge portion of said detection lens; and light intercepting means moving means for moving said light intercepting means.

45. A birefringence measuring apparatus as defined in claim 39, further comprising:

light intercepting means for intercepting light transmitted through a circumferential edge portion of said detection lens; and light intercepting means moving means for moving said light intercepting means.

46. A birefringence measuring apparatus comprising:

a radiation optical system means for radiating diffusion light onto a detection lens in a predetermined polarization state;

displacement means for moving and adjusting a position in an optical axis direction of said radiation optical system means with respect to said detection lens;

polarization element means for changing the polarization state of transmission light transmitted from said detection lens;

rotation means for rotating said polarization element means around an advancing direction of said transmission light;

rotation angle detection means for detecting an angle of rotating said polarization element means by said rotation means;

array-state light-receiving element means for receiving light transmitted through said polarization element means;

focusing optical system means for changing a focusing magnification of the light transmitted through said polarization element means and which is focused on said array-state light-receiving element means;

light-receiving-side displacement means for moving and adjusting a unitary combination of said polarization element means, said rotation means, said array-state light-receiving element means, and said focusing optical system means in a direction substantially perpendicular to the optical axis; and operational calculation means for calculating birefringence of said detection lens based on the rotation angle detected by said rotation angle detecting means and an output of the light which is focused on said array-state light-receiving element means.

47. A birefringence measuring apparatus comprising:

radiation optical system means for radiating diffusion light onto a detection lens in a predetermined polarization state;

displacement means for moving and adjusting a position of said radiation optical system means in an optical axis direction with respect to said detection lens;

a plurality of light-receiving units constructed, as one unit, with a polarization element means for changing the polarization state of transmission light from said detection lens, a rotation means for rotating said polarization element means around an advancing direction of said transmission light, a rotation angle detection means for detecting an angle of rotating said polarization element means by said rotation means, an array-state light-receiving element means for receiving transmission light transmitted through said polarization element means, and a focusing optical system means for changing a focusing magnification of light transmitted through said polarization element means and which is focused on a light-receiving surface of said array-state light-receiving element means;

branching means for branching transmission light from said detection lens and directing said branched transmission light as incident light to respective of said light-receiving units; and operational calculation means for calculating birefringence of said detection lens based on the rotation angle detected by said rotation angle detecting means and an output of the light which is focused on said array-state light-receiving element means.

48. A birefringence measuring apparatus as defined in claim 47, wherein said respective light-receiving units are arranged through said branching means to respectively receive light transmitted from different areas to be measured of said detection lens.

49. A birefringence measuring apparatus as defined in claim 47, wherein in said focusing optical system means, the focusing magnification is independently changed per each of said respective light-receiving units.

50. A birefringence measuring apparatus as defined claim 48, wherein in said focusing optical system means, the focusing magnification is independently changed per each of said respective light-receiving units.

51. A birefringence measuring apparatus as defined in claim 46, wherein, in said focusing optical system means, the focusing magnification is automatically set based on a transmission image from said detection lens obtained at a time of focusing the transmission light from said detection lens on the light-receiving surface of said array-state light-receiving element means.

52. A birefringence measuring apparatus as defined in claim 49, wherein, in said focusing optical system means, the focusing magnification is automatically set based on a transmission image from said detection lens obtained at a time of focusing the transmission light from said detection lens on the light-receiving surface of said array-state light-receiving element means.

53. A birefringence measuring apparatus as defined in claim 50, wherein, in said focusing optical system, the focusing magnification is automatically set based on a transmission image from said detection lens obtained at a time of focusing the transmission light from said detection lens on the light-receiving surface of said array-state light-receiving element means.

54. A birefringence measuring apparatus comprising:

radiation optical system means for radiating diffusion light onto a detection lens in a predetermined polarization state;

displacement means for moving and adjusting a position of said radiation optical system means in a direction of an optical axis from said detection lens;

compensation optical system means disposed at a radiation side of said detection lens for converting transmission light transmitted through the detection lens to substantially parallel light;

polarization element means for changing the polarization state of the transmission light from said detection lens;

rotation means for rotating said polarization element around an advancing direction of said transmission light;

rotation angle detection means for detecting an angle of rotating said polarization element means by said rotation means;

array-state light-receiving element means for receiving light transmitted through said polarization element means;

focusing optical system means for changing a focusing magnification of the light transmitted through said polarization element means and which is focused onto a light-receiving surface of said array-state light-receiving element means; and operational calculation means for calculating birefringence of said detection lens based on the rotation angle detected by said rotation angle detecting means and an output of the light which is focused on said array-state light-receiving element means.

55. A birefringence measuring apparatus as defined in claim 54, wherein said compensation optical system means is composed of a combination of plural optical elements respectively having different optical properties.

56. A birefringence measuring apparatus is defined in claim 54, further comprising:

lens displacement means for moving and adjusting said detection lens in a direction perpendicular to the optical axis.

57. A birefringence measuring apparatus as defined in claim 55, further comprising:

lens displacement means for moving and adjusting said detection lens in a direction perpendicular to the optical axis.

* * * * *